(12) United States Patent
Mitsuoka et al.

(10) Patent No.: US 9,315,535 B2
(45) Date of Patent: Apr. 19, 2016

(54) NUCLEOSIDE AND NUCLEOTIDE HAVING NITROGEN-CONTAINING HETEROCYCLE STRUCTURE

(71) Applicant: SHIONOGI & CO., LTD., Osaka-shi, Osaka (JP)

(72) Inventors: Yasunori Mitsuoka, Toyonaka (JP); Akira Kugimiya, Toyonaka (JP); Aiko Yamashita, Toyonaka (JP)

(73) Assignee: SHIONOGI & CO., LTD., Osaka-shi (JP)

( * ) Notice: Subject to any disclaimer, the term of this patent is extended or adjusted under 35 U.S.C. 154(b) by 0 days.

(21) Appl. No.: 14/766,827

(22) PCT Filed: Feb. 17, 2014

(86) PCT No.: PCT/JP2014/053580
§ 371 (c)(1),
(2) Date: Aug. 10, 2015

(87) PCT Pub. No.: WO2014/126229
PCT Pub. Date: Aug. 21, 2014

(65) Prior Publication Data
US 2015/0368287 A1 Dec. 24, 2015

(30) Foreign Application Priority Data
Feb. 18, 2013 (JP) ................. 2013-028923

(51) Int. Cl.
*C07H 19/10* (2006.01)
*C07H 19/06* (2006.01)
*C07H 19/16* (2006.01)
*C07H 21/00* (2006.01)

(52) U.S. Cl.
CPC .............. *C07H 19/10* (2013.01); *C07H 19/06* (2013.01); *C07H 19/16* (2013.01); *C07H 21/00* (2013.01); *Y02P 20/55* (2015.11)

(58) Field of Classification Search
None
See application file for complete search history.

(56) References Cited

U.S. PATENT DOCUMENTS

| 6,268,490 B1 | 7/2001 | Imanishi et al. |
| 6,403,566 B1 | 6/2002 | Wang |
| RE44,779 E | 2/2014 | Imanishi et al. |
| 8,846,637 B2 * | 9/2014 | Seth .................... C07H 19/073 514/45 |
| 2003/0105309 A1 | 6/2003 | Imanishi et al. |
| 2006/0166908 A1 | 7/2006 | Imanishi et al. |
| 2007/0167387 A1 | 7/2007 | Imanishi et al. |
| 2012/0208991 A1 | 8/2012 | Obika et al. |

FOREIGN PATENT DOCUMENTS

| EP | 2 899 197 A1 | 7/2015 |
| JP | 2002-516256 A | 6/2002 |
| WO | WO 98/39352 A1 | 9/1998 |
| WO | WO 03/068795 A1 | 8/2003 |
| WO | WO 2005/021570 A1 | 3/2005 |
| WO | WO 2010/021344 A1 | 2/2010 |
| WO | WO 2011/052436 A1 | 5/2011 |
| WO | WO 2011/156202 A1 | 12/2011 |
| WO | WO 2014/046212 A1 | 3/2014 |

OTHER PUBLICATIONS

Hari et al., "Synthesis and properties of 2'-0,4'-C-Methyleneoxymethylene bridged nucleic acid", Bioorganic & Medicinal Chemistry, 2006, vol. 14, pp. 1029-1038.
International Search Report, issued in PCT/JP2014/053580, dated May 20, 2014.
Kuwahara et al., "Systematic analysis of enzymatic DNA polymerization using oligo-DNA templates and triphosphate analogs involving 2',4'-bridged nucleosides", Nucleic Acids Research, 2008, vol. 36, No. 13, pp. 4257-4265.

(Continued)

*Primary Examiner* — Traviss C McIntosh, III
(74) *Attorney, Agent, or Firm* — Birch, Stewart, Kolasch & Birch, LLP

(57) ABSTRACT

The present invention provides compounds shown by the formula:

(I)

wherein
$Y^1$ is $CR^6$ or N,
$Y^2$ is $CR^7$ or N,
$Y^3$ is $CR^8$ or N,
$R^6$, $R^7$ and $R^8$ are each independently, a hydrogen atom, halogen, cyano, substituted or unsubstituted alkyl or the like,
Bx is a nucleic acid base moiety,
$Z^1$ and $Z^2$ are each independently, a hydrogen atom, a hydroxyl protecting group or a reactive phosphorus group,
$R^1$ to $R^5$ are each independently, a hydrogen atom, halogen, cyano, substituted or unsubstituted alkyl or the like, and
n is an integer of 0 to 3,
or salts thereof, that are novel nucleosides or nucleotides that can be useful as materials for synthesizing nucleic acid pharmaceuticals.

20 Claims, 1 Drawing Sheet

(56) References Cited

OTHER PUBLICATIONS

Miyashita et al., "N-Methyl substituted 2',4'-BNANC: a highly nuclease-resistant nucleic acid analogue with high-affinity RNA selective hybridization", Chem. Commun., 2007, pp. 3765-3767.
Obika et al., "2'-0,4'-C-Methylene Bridged Nucleic Acid (2',4'-BNA): Synthesis and Triplex-Forming Properties1", Bioorganic & Medicinal Chemistry, 2001, vol. 9, pp. 1001-1011.
Rahman et al., "Design, Synthesis, and Properties of 2',4'-BNANC: A Bridged Nucleic Acid Analogue", J. Am. Chem. Soc., 2008, vol. 130, No. 14, pp. 4886-4896.
Wahlestedt et al., "Potent and nontoxic antisense oligonucleotides containing locked nucleic acids", Proc. Natl. Acad. Sci. USA, 2000, vol. 97, No. 10, pp. 5633-5638.
Written Opinion of the International Searching Authority, issued in PCT/JP2014/053580, dated May 20, 2014.

* cited by examiner

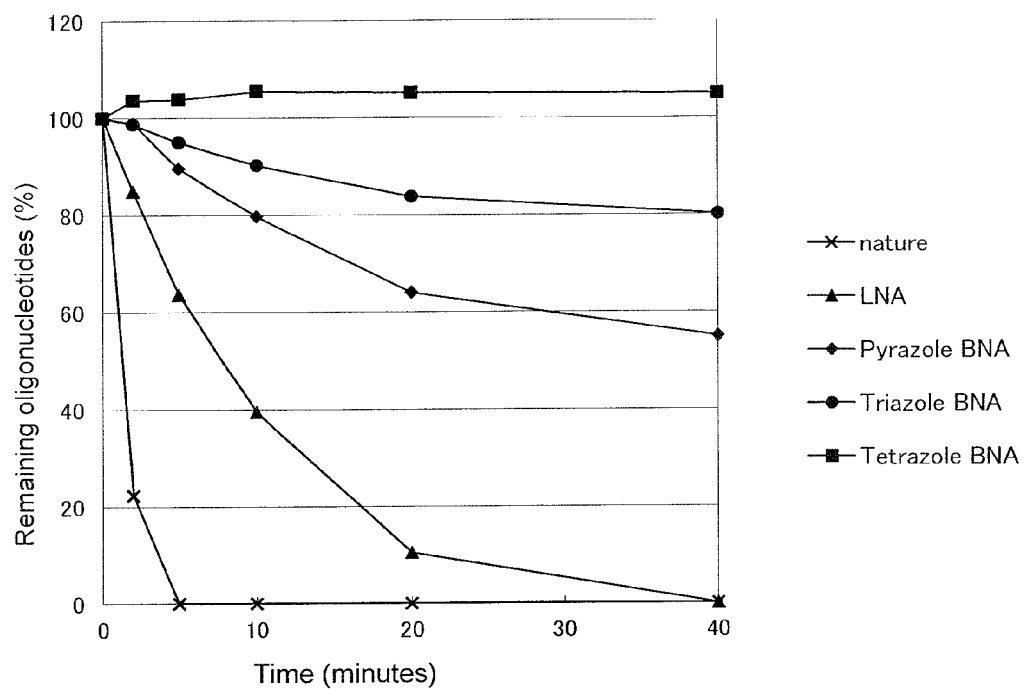

NUCLEOSIDE AND NUCLEOTIDE HAVING NITROGEN-CONTAINING HETEROCYCLE STRUCTURE

FIELD OF THE INVENTION

The present invention relates to a novel bridged nucleoside or nucleotide. In more detail, it relates to a nucleoside or nucleotide having a bridge comprising a nitrogen-containing heterocycle structure, or an oligonucleotide prepared with the nucleoside(s) or nucleotide(s).

BACKGROUND ART

As a therapy for a disease with a nucleic acid pharmaceutical, there is a method with an antisense oligonucleotide, siRNA, ribozyme, antigene, aptamer, decoy nucleic acid or the like.

An antisense oligonucleotide is an oligonucleotide complementary to mRNA, mRNA precursor or ncRNA (non-coding RNA), such as ribosomal RNA, transfer RNA, miRNA and the like, of the target gene, and a single strand DNA, RNA and/or structural analog thereof which consists of about 8 to 30 bases. The antisense oligonucleotide suppresses the function of mRNA, mRNA precursor or ncRNA by forming a double strand with the target mRNA, mRNA precursor or ncRNA.

A siRNA is a low molecular weight double-strand RNA complementary to the target gene which consists of about 19 to 25 base pairs. It relates to a phenomenon called RNA interference, and suppresses the gene expression by base sequence-specific mRNA degradation.

A ribozyme is RNA with enzyme activity of cleaving a nucleic acid. It cleaves specifically the mRNA of the target gene by forming double strands with the mRNA.

An antigene is an oligonucleotide corresponding to a double strand DNA moiety of the target gene. It suppresses transcription from the DNA to mRNA by forming triple strands with the DNA moiety and oligonucleotide.

An aptamer is a DNA, RNA and/or structural analog thereof which specifically bonds to a specific molecule. It inhibits the function of the target protein by binding to the protein.

A decoy nucleic acid is a short DNA comprising the same sequence with a binding site for a specific transcription modulating factor. It inhibits binding with the transcription modulating factor and gene, and suppresses expression of the gene groups activated by the transcription modulating factor.

Various nucleosides or nucleotides are developed as materials for synthesizing the above nucleic acid pharmaceuticals. Examples include S-oligo (phosphorothioate) which is modified the phosphate moiety of a nucleotide, 2',4'-BNA (bridged nucleic acid)/LNA (locked nucleic acid) which is modified the sugar moiety of a nucleoside or nucleotide (Patent Documents 1 to 5 and Non-patent Documents 1 to 6) and the like.

PRIOR ART DOCUMENT

Patent Document

[Patent Document 1] WO98/39352
[Patent Document 2] WO2005/021570
[Patent Document 3] WO2003/068795
[Patent Document 4] WO2011/052436
[Patent Document 5] WO2011/156202

Non-Patent Document

[Non-patent Document 1] Proc. Natl. Acad. Sci. USA, 2000, vol. 97, no. 10, 5633-5638
[Non-patent Document 2] Bioorg. Med. Chem., 2006, vol. 14, 1029-1038
[Non-patent Document 3] Chem. Commun., 2007, 3765-3767
[Non-patent Document 4] J. Am. Chem. Soc., 2008, vol. 130, no. 14, 4886-4896
[Non-patent Document 5] Nucleic Acids Res., 2008, vol. 36, no. 13, 4257-4265
[Non-patent Document 6] Bioorg. Med. Chem., 2001, vol. 9, 1001-1011

SUMMARY OF THE INVENTION

Problems to be Solved by the Invention

The present invention is intended to provide novel nucleosides or nucleotides that can be useful as materials for synthesizing nucleic acid pharmaceuticals such as antisense oligonucleotides, siRNAs, ribozymes, antigenes, aptamers, decoy nucleic acids and the like.

Means for Solving the Problem

The present inventors have intensively studied to synthesize novel bridged nucleosides or nucleotides with the superior binding affinity to a single strand RNA and nuclease resistance. Using the nucleoside(s) or nucleotide(s), oligonucleotide(s) can be synthesized stably without by-products by general methods for synthesizing. The nucleosides or nucleotides are useful very much as materials for synthesizing nucleic acid pharmaceuticals (pharmaceutical compositions) such as antisense oligonucleotides and the like.

That is, this invention is related to the following.

(1) A compound of formula (I) or a salt thereof

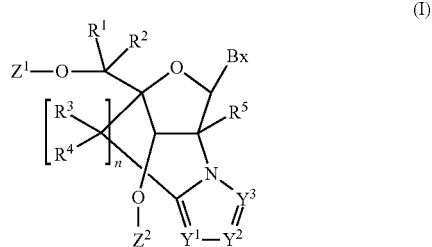

wherein
$Y^1$ is $CR^6$ or N,
$Y^2$ is $CR^7$ or N,
$Y^3$ is $CR^8$ or N,
$R^6$, $R^7$ and $R^8$ are each independently, a hydrogen atom, halogen, cyano, substituted or unsubstituted alkyl, substituted or unsubstituted alkenyl, substituted or unsubstituted alkynyl, substituted or unsubstituted amino, substituted or unsubstituted alkoxy, substituted or unsubstituted alkylcarbonylamino, substituted or unsubstituted alkenylcarbonylamino, substituted or unsubstituted alkynylcarbonylamino, substituted or unsubstituted alkylcarbamoyl, substituted or unsubstituted alkenylcarbamoyl, or substituted or unsubstituted alkynylcarbamoyl,
Bx is a nucleic acid base moiety,
$Z^1$ and $Z^2$ are each independently, a hydrogen atom, a hydroxyl protecting group or a reactive phosphorus group,
$R^1$ and $R^2$ are each independently, a hydrogen atom, halogen, cyano, substituted or unsubstituted alkyl, substituted or unsubstituted alkenyl, or substituted or unsubstituted alkynyl, $R^3$ are each independently, a hydrogen atom, halogen, cyano, substituted or unsubstituted alkyl, substituted or unsubstituted alkenyl, or substituted or unsubstituted alkynyl, $R^4$ are each independently, a hydrogen atom, halogen, cyano, substituted or unsubstituted alkyl, substituted or unsubstituted alkenyl, or substituted or unsubstituted alkynyl, $R^5$ is a hydrogen atom, halogen, cyano, substituted or unsubstituted alkyl, substituted or unsubstituted alkenyl, or substituted or unsubstituted alkynyl, and n is an integer of 0 to 3.

(2) The compound or salt thereof of (1), wherein a group of the formula:

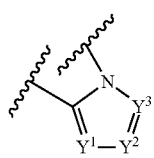

is a group of the formula:

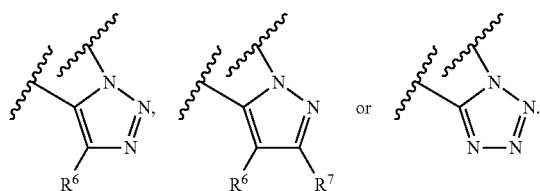

(3) The compound or salt thereof of (1) or (2), wherein Bx is substituted or unsubstituted purin-9-yl, or substituted or unsubstituted 2-oxo-pyrimidin-1-yl.

(4) The compound or salt thereof of any one of (1) to (3), wherein $Z^1$ is a hydrogen atom or hydroxyl protecting group.

(5) The compound or salt thereof of (4), wherein the hydroxyl protecting group is acetyl, t-butyl, t-butoxymethyl, methoxymethyl, tetrahydropyranyl, 1-ethoxyethyl, 1-(2-chloroethoxy)-ethyl, 2-trimethylsilylethyl, p-chlorophenyl, 2,4-dinitrophenyl, benzyl, benzoyl, p-phenylbenzoyl, 2,6-dichlorobenzyl, levulinoyl, diphenylmethyl, p-nitrobenzyl, trimethylsilyl, triethylsilyl, t-butyldimethylsilyl, t-butyldiphenylsilyl, triphenylsilyl, triisopropylsilyl, benzoyl formate, chloroacetyl, trichloroacetyl, trifluoroacetyl, pivaloyl, isobutyryl, 9-fluorenylmethyloxycarbonyl, methansulfonyl, p-toluenesulfonyl, trifluoromethanesulfonyl, trityl, monomethoxytrityl, dimethoxytrityl, trimethoxytrityl, 9-phenylxanthin-9-yl or 9-(p-methoxyphenyl)xanthin-9-yl.

(6) The compound or salt thereof of any one of (1) to (5), wherein $Z^2$ is a hydrogen atom or reactive phosphorus group.

(7) The compound or salt thereof of (6), wherein the reactive phosphorus group is diisopropylcyanoethoxy phosphoramidite or H-phosphonate.

(8) An oligonucleotide comprising one or more nucleoside structure of formula (II) or a pharmaceutically acceptable salt thereof.

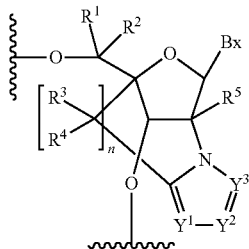

wherein
$Y^1$ is $CR^6$ or N,
$Y^2$ is $CR^7$ or N,
$Y^3$ is $CR^8$ or N,
$R^6$, $R^7$ and $R^8$ are each independently, a hydrogen atom, halogen, cyano, substituted or unsubstituted alkyl, substituted or unsubstituted alkenyl, substituted or unsubstituted alkynyl, substituted or unsubstituted amino, substituted or unsubstituted alkoxy, substituted or unsubstituted alkylcarbonylamino, substituted or unsubstituted alkenylcarbonylamino, substituted or unsubstituted alkynylcarbonylamino, substituted or unsubstituted alkylcarbamoyl, substituted or unsubstituted alkenylcarbamoyl, or substituted or unsubstituted alkynylcarbamoyl,
Bx is a nucleic acid base moiety,
$R^1$ and $R^2$ are each independently, a hydrogen atom, halogen, cyano, substituted or unsubstituted alkyl, substituted or unsubstituted alkenyl, or substituted or unsubstituted alkynyl,
$R^3$ are each independently, a hydrogen atom, halogen, cyano, substituted or unsubstituted alkyl, substituted or unsubstituted alkenyl, or substituted or unsubstituted alkynyl,
$R^4$ are each independently, a hydrogen atom, halogen, cyano, substituted or unsubstituted alkyl, substituted or unsubstituted alkenyl, or substituted or unsubstituted alkynyl,
$R^5$ is a hydrogen atom, halogen, cyano, substituted or unsubstituted alkyl, substituted or unsubstituted alkenyl, or substituted or unsubstituted alkynyl, and
n is an integer of 0 to 3.

Effect of the Invention

An oligonucleotide prepared with the nucleotide(s) or nucleoside(s) of the present invention shows the superior binding affinity to a single strand RNA and nuclease resistance. The oligonucleotide is thought to have very good persistence in vivo, and therefore expected to apply to nucleic acid pharmaceuticals.

BRIEF DESCRIPTION OF THE DRAWINGS

FIG. 1 A graph showing the exonuclease resistant properties of the oligonucleotides of the present invention. (Example 4)

EMBODIMENTS FOR CARRYING OUT THE INVENTION

Terms used herein, unless otherwise indicated, are used in a sense normally used in the art.

Terms used in this description are explained below. Each term, unless otherwise indicated, has the same meaning when it is used alone or together with other terms.

The term "nucleic acid base moiety" means a substituent containing a nucleic acid base or an analog thereof. Examples of natural nucleic acid bases include adenine (A), guanine (G), thymine (T), cytosine (C) and uracil (U). The nucleic acid base of the present invention is not limited to them, and includes the other artificial or natural nucleic acid bases. Examples include 5-methylcytosine (5-me-C), 5-hydroxymethylcytosine, xanthine, hypoxanthine, 2-aminoadenine, 7-deaza-adenine, 7-deazaguanosine, 2-aminopyridine, 2-pyridone and the like.

In other words, the "nucleic acid base moiety" for the present invention is substituted or unsubstituted heterocyclyl, or substituted or unsubstituted carbocyclyl which constitutes a base moiety of a nucleic acid (DNA or RNA).

The heterocycle includes monocycle or polycycle, containing one or more of heteroatom(s) selected independently from O, S and N. Examples include purine, pyrimidine, thiophene, thianthrene, furan, pyran, isobenzofuran, chromene, xanthene, phenoxathiin, pyrrole, imidazole, pyrazole, isothiazole, isoxazole, pyridazine, indolizine, indole, isoindole, isoquinoline, quinoline, naphthyridine, quinoxaline, quinazoline, pteridine, carbazole, phenanthridine, acridine, perimidine, phenazine, phenarsazine, phenothiazine, furazan, phenoxazine, pyrrolidine, pyrroline, imidazolidine, imidazoline, pyrazolidine and the like. Preferably it is purine or pyrimidine.

The carbocycle includes monocyclic or polycyclic hydrocarbocycle. Examples include benzene, naphthalene, anthracene, phenanthrene, indane, indene, tetrahydronaphthalene, biphenylene and the like. Preferably, it is benzene or naphthalene, The substituent for the heterocyclyl or carbocyclyl is a substituent selected from Substituent group α. A carbon atom at any position may bind to one or more substituent(s) selected from Substituent group α.

Substituent group α: halogen, hydroxy, a hydroxyl group protected with a protective group for synthesis of nucleic acid, alkyl, alkyloxy, alkylthio, alkylamino, alkenyl, alkynyl, mercapto, a mercapto group protected with a protective group for synthesis of nucleic acid, amino, and an amino group protected with a protective group for synthesis of nucleic acid.

The protective group for "a hydroxyl group protected with a protective group for synthesis of nucleic acid" is not limited, as long as it can stably protect a hydroxyl group during synthesis of nucleic acid. Concretely, it is a protective group which is stable under acidic or neutral conditions and which can be cleft by a chemical method such as hydrogenolysis, hydrolysis, electrolysis or photolysis. Examples include substituted or unsubstituted alkyl, substituted or unsubstituted alkenyl, formyl or the following protective groups.

Aliphatic acyl: alkylcarbonyl such as acetyl, propionyl, butyryl, isobutyryl, pentanoyl, pivaloyl, valeryl, isovaleryl, octanoyl, nonanoyl, decanoyl, 3-methylnonanoyl, 8-methylnonanoyl, 3-ethyloctanoyl, 3,7-dimethyloctanoyl, undecanoyl, dodecanoyl, tridecanoyl, tetradecanoyl, pentadecanoyl, hexadecanoyl, 1-methylpentadecanoyl, 14-methylpentadecanoyl, 13,13-dimethyltetradecanoyl, heptadecanoyl, 15-methylhexadecanoyl, octadecanoyl, 1-methylheptadecanoyl, nonadecanoyl, eicosanoyl, heneicosanoyl and the like, carboxylated alkylcarbonyl such as succinoyl, glutaroyl, adipoyl and the like, haloalkylcarbonyl such as chloroacetyl, dichloroacetyl, trichloroacetyl, trifluoroacetyl and the like, alkyloxyalkylcarbonyl such as methoxyacetyl and the like, and unsaturated alkylcarbonyl such as (E)-2-methyl-2-butenoyl and the like, etc.

Aromatic acyl: arylcarbonyl such as benzoyl, α-naphthoyl, β-naphthoyl and the like, halogenoarylcarbonyl such as 2-bromobenzoyl, 4-chlorobenzoyl and the like, alkylated arylcarbonyl such as 2,4,6-trimethylbenzoyl, 4-toluoyl and the like, alkyloxylated arylcarbonyl such as 4-anisoyl and the like, carboxylated arylcarbonyl such as 2-carboxybenzoyl, 3-carboxybenzoyl, 4-carboxybenzoyl and the like, nitrated arylcarbonyl such as 4-nitrobenzoyl, 2-nitrobenzoyl and the like, alkyloxycarbonylated arylcarbonyl such as 2-(methoxycarbonyl)benzoyl and the like, and arylated arylcarbonyl such as 4-phenylbenzoyl and the like, etc.

Tetrahydropyranyl: tetrahydropyran-2-yl, 3-bromotetrahydropyran-2-yl, 4-methoxytetrahydropyran-4-yl and the like.

Tetrahydrothiopyranyl: tetrahydrothiopyran-2-yl, 4-methoxytetrahydrothiopyran-4-yl and the like.

Tetrahydrofuranyl: tetrahydrofuran-2-yl and the like.

Tetrahydrothiofuranyl: tetrahydrothiofuran-2-yl and the like.

Silyl: trialkylsilyl such as trimethylsilyl, triethylsilyl, isopropyldimethylsilyl, t-butyldimethylsilyl, methyldiisopropylsilyl, methyl di-t-butylsilyl, triisopropylsilyl and the like, trialkylsilyl substituted by one or two aryl such as diphenylmethylsilyl, diphenylbutylsilyl, diphenylisopropylsilyl, phenyldiisopropylsilyl and the like, etc.

Alkyloxymethyl: methoxymethyl, 1,1-dimethyl-1-methoxymethyl, ethoxymethyl, propoxymethyl, isopropoxymethyl, butoxymethyl, t-butoxymethyl and the like.

Alkyloxylated alkyloxymethyl: 2-methoxyethoxymethyl and the like.

Halogeno alkyloxymethyl: 2,2,2-trichloroethoxymethyl, bis (2-chloroethoxy)methyl and the like.

Alkyloxylated ethyl: 1-ethoxyethyl, 1-(isopropoxy)ethyl and the like.

Halogenated ethyl: 2,2,2-trichloroethyl and the like.

Methyl substituted by 1 to 3 aryl: benzyl, α-naphthylmethyl, β-naphthylmethyl, diphenylmethyl, triphenylmethyl, α-naphthyldiphenylmethyl, 9-anthrylmethyl and the like.

Methyl substituted by 1 to 3 aryl, with the aryl ring being substituted by alkyl, alkyloxy, halogen or cyano: 4-methylbenzyl, 2,4,6-trimethylbenzyl, 3,4,5-trimethylbenzyl, 4-methoxybenzyl, 4-methoxyphenyldiphenylmethyl, 4,4'-dimethoxytriphenylmethyl, 2-nitrobenzyl, 4-nitrobenzyl, 4-chlorobenzyl, 4-bromobenzyl, 4-cyanobenzyl and the like.

Alkyloxycarbonyl: methoxycarbonyl, ethoxycarbonyl, t-butoxycarbonyl, isobutoxycarbonyl and the like.

Aryl substituted by halogen, alkyloxy or nitro: 4-chlorophenyl, 2-fluorophenyl, 4-methoxyphenyl, 4-nitrophenyl, 2,4-dinitrophenyl and the like.

Alkyloxycarbonyl substituted by halogen or trialkylsilyl: 2,2,2-trichloroethoxycarbonyl, 2-trimethylsilylethoxycarbonyl and the like.

Alkenyloxycarbonyl: vinyloxycarbonyl, aryloxycarbonyl and the like.

Aralkyloxycarbonyl having an aryl ring optionally substituted by one or two alkyloxy or nitro: benzyloxycarbonyl, 4-methoxybenzyloxycarbonyl, 3,4-dimethoxybenzyloxycarbonyl, 2-nitrobenzyloxycarbonyl, 4-nitrobenzyloxycarbonyl and the like.

A preferable protective group is alkyl, alkenyl, "aliphatic acyl", "aromatic acyl", "methyl substituted by 1 to 3 aryl", "aryl substituted by halogen, alkyloxy or nitro" or the like. More preferably, it is benzoyl, benzyl, 2-chlorophenyl, 4-chlorophenyl, 2-propenyl or the like.

The protective group for "a mercapto group protected with a protective group for synthesis of nucleic acid" is not limited, as long as it can stably protect a mercapto group during synthesis of nucleic acid. Concretely, it is a protective group which is stable under acidic or neutral conditions and which can be cleft by a chemical method such as hydrogenolysis, hydrolysis, electrolysis or photolysis.

Examples include not only those named above as the protective group for a hydroxyl group, but also the following. Disulfide-forming groups: alkylthio such as methylthio, ethylthio, tert-butylthio and the like, arylthio such as benzylthio and the like, etc.

A preferable protective group is "aliphatic acyl", "aromatic acyl" and the like. More preferably, it is benzoyl or the like.

The protective group for "an amino group protected with a protective group for synthesis of nucleic acid" is not limited, as long as it can stably protect an amino group during synthesis of nucleic acid. Concretely, it is a protective group which is stable under acidic or neutral conditions and which can be cleft by a chemical method such as hydrogenolysis, hydrolysis, electrolysis or photolysis.

Examples include formyl and the above protective groups for the hydroxyl group, such as "aliphatic acyl", "aromatic acyl", "alkyloxycarbonyl", "alkyloxycarbonyl substituted by halogen or trialkylsilyl", "alkenyloxycarbonyl" and "aralkyloxycarbonyl having an aryl ring optionally substituted by one or two alkyloxy or nitro".

A preferable protective group is "aliphatic acyl", "aromatic acyl" or the like. More preferably, it is benzoyl or the like.

The "nucleic acid base moiety" is preferably substituted or unsubstituted purin-9-yl, substituted or unsubstituted 2-oxo-pyrimidin-1-yl or the like. The substituent for a ring containing a nucleic acid base moiety is a substituent selected from the above Substituent group α. A carbon atom at any position may bind to one or more substituent(s) selected from Substituent group α. More preferably, it is purin-9-yl or 2-oxo-pyrimidin-1-yl substituted by one or more substituent(s) selected from the above Substituent group α. Especially preferably, it is purin-9-yl or 2-oxo-pyrimidin-1-yl substituted by one or two substituent(s) selected from the above Substituent group α.

Examples include 6-aminopurin-9-yl (i.e. adeninyl), 6-aminopurin-9-yl having an amino group protected with a protective group for synthesis of nucleic acid, 2,6-diaminopurin-9-yl, 2,6-diaminopurin-9-yl having an amino group protected with a protective group for synthesis of nucleic acid, 6-chloropurin-9-yl, 2-amino-6-chloropurin-9-yl, 2-amino-6-chloropurin-9-yl having an amino group protected with a protective group for synthesis of nucleic acid, 6-fluoropurin-9-yl, 2-amino-6-fluoropurin-9-yl, 2-amino-6-fluoropurin-9-yl having an amino group protected with a protective group for synthesis of nucleic acid, 6-bromopurin-9-yl, 2-amino-6-bromopurin-9-yl, 2-amino-6-bromopurin-9-yl having an amino group protected with a protective group for synthesis of nucleic acid, 2-amino-6-hydroxypurin-9-yl (i.e. guaninyl), 2-amino-6-hydroxypurin-9-yl having an amino group protected with a protective group for synthesis of nucleic acid, 6-amino-2-methoxypurin-9-yl, 6-amino-2-chloropurin-9-yl, 6-amino-2-fluoropurin-9-yl, 2,6-dimethoxypurin-9-yl, 2,6-dichloropurin-9-yl, 6-mercaptopurin-9-yl, 2-oxo-4-amino-1,2-dihydropyrimidin-1-yl (i.e. cytosinyl), 2-oxo-4-amino-1,2-dihydropyrimidin-1-yl having an amino group protected with a protective group for synthesis of nucleic acid, 2-oxo-4-amino-5-fluoro-1,2-dihydropyrimidin-1-yl, 2-oxo-4-amino-5-fluoro-1,2-dihydropyrimidin-1-yl having an amino group protected with a protective group for synthesis of nucleic acid, 4-amino-2-oxo-5-chloro-1,2-dihydropyrimidin-1-yl, 2-oxo-4-methoxy-1,2-dihydropyrimidin-1-yl, 2-oxo-4-mercapto-1,2-dihydropyrimidin-1-yl, 2-oxo-4-hydroxy-1,2-dihydropyrimidin-1-yl (i.e. uracinyl), 2-oxo-4-hydroxy-5-methyl-1,2-dihydropyrimidin-1-yl (i.e. thyminyl), 4-amino-5-methyl-2-oxo-1,2-dihydropyrimidin-1-yl (i.e. 5-methyl cytosinyl), 4-amino-5-methyl-2-oxo-1,2-dihydropyrimidin-1-yl having an amino group protected with a protective group for synthesis of nucleic acid and the like.

More concretely, groups of formula: (B-1) to (B-4) described below are exemplified.

A group of formula (B-1):

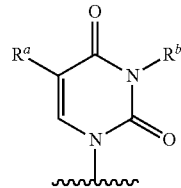

(B-1)

wherein
$R^a$ is a hydrogen atom or alkyl, and
$R^b$ is a hydrogen atom or alkyl.
$R^a$ is preferably a hydrogen atom or C1 to C5 alkyl. A hydrogen atom or methyl is more preferable.
$R^b$ is preferably a hydrogen atom.

A group of formula (B-2):

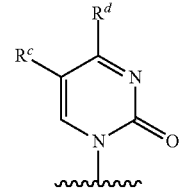

(B-2)

wherein
$R^c$ is a hydrogen atom, halogen or alkyl,
$R^d$ is amino, mercapto, alkyloxy, NHCOR$^e$, NHCOCH$_2$ OR$^e$ or N=NR$^f$,
$R^e$ is substituted or unsubstituted alkyl, or substituted or unsubstituted aromatic carbocyclyl, and
$R^f$ is a hydrogen atom or alkyl.
$R^c$ is preferably a hydrogen atom or C1 to C5 alkyl. A hydrogen atom or methyl is more preferable.
$R^d$ is preferably NHCOPh, NHCOCH$_3$, NHCOCH$_2$ OPh or NHCOCH$_2$O-(4-tBu)Ph.

A group of formula (B-3):

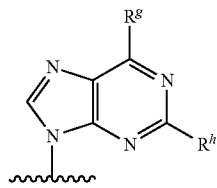

(B-3)

wherein
$R^g$ is halogen, amino, mercapto, alkyloxy, NHCOR$^i$, NHCOCH$_2$ OR$^i$ or N=NR$^j$,
$R^h$ is a hydrogen atom, halogen, amino or alkyloxy,
$R^i$ is substituted or unsubstituted alkyl, or substituted or unsubstituted aromatic carbocyclyl, and
$R^j$ is a hydrogen atom or alkyl.
$R^g$ is preferably NHCOPh, NHCOCH$_3$, NHCOCH$_2$ OPh or NHCOCH$_2$O-(4-tBu)Ph.
$R^h$ is preferably a hydrogen atom.

A group of formula (B-4):

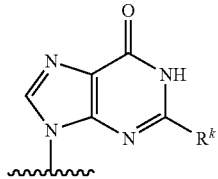

wherein
$R^k$ is amino, NHCOR''', NHCOCH$_2$ OR''' or N=NR'',
R''' is substituted or unsubstituted alkyl, or substituted or unsubstituted aromatic carbocyclyl, and
R'' is a hydrogen atom or alkyl.

$R^k$ is preferably NHCOPh, NHCOCH$_3$, NHCOCH(CH$_3$)$_2$, NHCOCH$_2$ OPh or NHCOCH$_2$O-(4-tBu)Ph.

Examples include as follows.

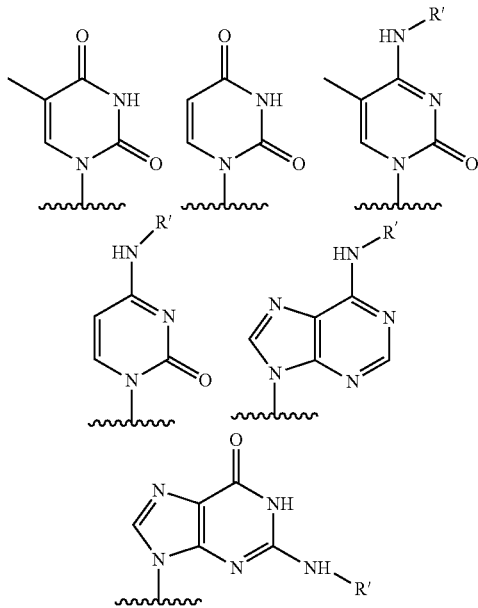

wherein R' is a hydrogen atom or a protecting group for amino used in nucleic acid synthesis. Examples include isobutyl, acetyl, benzoyl, phenoxyacetyl and the like.

The term "hydroxyl protecting group" for $Z^1$ and $Z^2$ includes those named above as "a hydroxyl group protected with a protective group for synthesis of nucleic acid". Preferably, it is alkyl, alkenyl, "aliphatic acyl", "aromatic acyl" or the like.

More preferably, it is acetyl, t-butyl, t-butoxymethyl, methoxymethyl, tetrahydropyranyl, 1-ethoxyethyl, 1-(2-chloroethoxyl)ethyl, 2-trimethylsilylethyl, p-chlorophenyl, 2,4-dinitrophenyl, benzyl, benzoyl, p-phenylbenzoyl, 2,6-dichlorobenzyl, levulinoyl, diphenylmethyl, p-nitrobenzyl, trimethylsilyl, triethylsilyl, t-butyldimethylsilyl, t-butyldiphenylsilyl, triphenylsilyl, triisopropylsilyl, benzoyl formate, chloroacetyl, trichloroacetyl, trifluoroacetyl, pivaloyl, isobutyryl, 9-fluorenylmethyloxycarbonyl, methansulfonyl, p-toluenesulfonyl, trifluoromethanesulfonyl, triphenylmethyl (trityl), monomethoxytrityl, dimethoxytrityl (DMTr), trimethoxytrityl, 9-phenylxanthin-9-yl (Pixyl) or 9-(p-methoxyphenyl)xanthin-9-yl (MOX). Especially preferably, it is benzyl, triethylsilyl, t-butyldimethylsilyl, t-butyldiphenylsilyl, triisopropylsilyl, trityl, monomethoxytrityl, dimethoxytrityl, trimethoxytrityl or the like.

The term "reactive phosphorus group" means a group containing phosphorous atom(s) which is (are) useful for forming an internucleoside linkage such as phosphodiester and phosphorotioate internucleoside linkages. The reactive phosphorous groups publicly known in the art can be used and examples include phosphoramidite, H-phosphonate, phosphate diesters, phosphate triesters, phosphorus containing chiral auxiliaries and the like.

Concretely, examples include groups of the following formula: $(Z^2$-1) to $(Z^2$-3).

A group of formula $(Z^2$-1): —P(OR$^{X1}$)(NR$^{X2}$) wherein $R^{X1}$ is substituted or unsubstituted alkyl and $R^{X2}$ is substituted or unsubstituted alkyl. $R^{X1}$ is preferably alkyl or cyanoalkyl. $R^{X2}$ is preferably alkyl.

A group of formula $(Z^2$-2): —P(=R$^{X3}$)(OR$^{X4}$)$_2$ wherein $R^{X3}$ is O or S, and $R^{X4}$ are each independently, a hydrogen atom, a protective group used in nucleic acid synthesis, substituted or unsubstituted alkyl, or substituted or unsubstituted aromatic carbocyclyl. $R^{X3}$ is preferably O, and $R^{X4}$ is preferably a hydrogen atom.

A group of formula $(Z^2$-3): —P(=R$^{X5}$)H(OR$^{X6}$) wherein $R^{X5}$ is O or S, and $R^{X6}$ is a hydrogen atom, a protective group used in nucleic acid synthesis, or substituted or unsubstituted aromatic carbocyclyl. $R^{X5}$ is preferably O, and $R^{X6}$ is preferably a hydrogen atom.

The term "protective group used in nucleic acid synthesis" for $R^{X4}$ and $R^{X6}$ includes those named above as "a hydroxyl group protected with a protective group for synthesis of nucleic acid". Preferably, it is alkyl, alkenyl, "aliphatic acyl", "aromatic acyl", "methyl substituted by 1 to 3 aryl", "aryl substituted by halogen, alkyloxy or nitro" or the like. More preferably, it is benzoyl, benzyl, 2-chlorophenyl, 4-chlorophenyl, 2-propenyl or the like.

The term reactive phosphorus group is especially preferably diisopropylcyanoethoxy phosphoramidite (a group of the formula: —P(OC$_2$H$_4$ CN)(N(i-Pr)$_2$)), H-phosphonate (a group of the formula: —P(=O)H(OH)) or the like.

The term "halogen" includes a fluorine atom, a chlorine atom, a bromine atom and an iodine atom. A fluorine atom and a chlorine atom are especially preferable.

The "alkyl" includes a C1 to C15, preferably a C1 to C10, more preferably a C1 to C6 and further preferably a C1 to C4 linear or branched hydrocarbon group. Examples include methyl, ethyl, n-propyl, isopropyl, n-butyl, isobutyl, sec-butyl, tert-butyl, n-pentyl, isopentyl, neopentyl, n-hexyl, isohexyl, n-heptyl, isoheptyl, n-octyl, isooctyl, n-nonyl, n-decyl and the like.

A preferred embodiment of "alkyl" is methyl, ethyl, n-propyl, isopropyl, n-butyl, isobutyl, sec-butyl, tert-butyl or n-pentyl. A more preferred embodiment is methyl, ethyl, n-propyl, isopropyl or tert-butyl.

The "alkenyl" includes a C2 to C15, preferably a C2 to C10, more preferably a C2 to C6 and further preferably a C2 to C4 linear or branched hydrocarbon group having one or more double bond(s) at any position(s). Examples include vinyl, allyl, propenyl, isopropenyl, butenyl, isobutenyl, prenyl, butadienyl, pentenyl, isopentenyl, pentadienyl, hexenyl, isohexenyl, hexadienyl, heptenyl, octenyl, nonenyl, decenyl, undecenyl, dodecenyl, tridecenyl, tetradecenyl, pentadecenyl and the like.

A preferred embodiment of "alkenyl" is vinyl, allyl, propenyl, isopropenyl or butenyl.

The term "alkynyl" includes a C2 to C10, preferably a C2 to C8, more preferably a C2 to C6 and further preferably a C2 to C4 linear or branched hydrocarbon group having one or more triple bond(s) at any position(s). Examples include ethynyl, propynyl, butynyl, pentynyl, hexynyl, heptynyl, octynyl, nonynyl, decynyl and the like. Furthermore, it may have double bond(s) at any position(s).

A preferred embodiment of "alkynyl" is ethynyl, propynyl, butynyl or pentynyl.

The term "aromatic carbocyclyl (aryl)" means a cyclic aromatic hydrocarbon group which is monocyclic or polycyclic having two or more rings. Examples include phenyl, naphthyl, anthryl, phenanthryl and the like.

A preferred embodiment of "aromatic carbocyclyl (aryl)" is phenyl.

The term "non-aromatic carbocyclyl" means a cyclic saturated hydrocarbon group or cyclic unsaturated non-aromatic hydrocarbon group, which is monocyclic or polycyclic having two or more rings. Examples of the non-aromatic carbocyclyl, which is polycyclic having two or more rings, include a fused ring group wherein a non-aromatic carbocyclyl, which is monocyclic or polycyclic having two or more rings, is fused with a ring of the above "aromatic carbocyclyl".

In addition, examples of the "non-aromatic carbocyclyl" also include a group having a bridge or a group to form a spiro ring as follows:

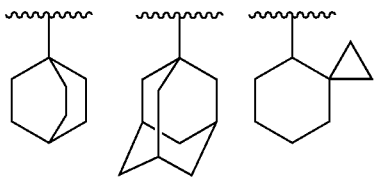

The non-aromatic carbocyclyl, which is monocyclic, is preferably C3 to C16, more preferably C3 to C12 and further preferably C4 to C8 carbocyclyl. Examples include cyclopropyl, cyclobutyl, cyclopentyl, cyclohexyl, cycloheptyl, cyclooctyl, cyclononyl, cyclodecyl, cyclopropenyl, cyclobutenyl, cyclopentenyl, cyclohexenyl, cycloheptenyl, cyclohexadienyl and the like.

Examples of non-aromatic carbocyclyl, which is polycyclic having two or more rings, include indanyl, indenyl, acenaphthyl, tetrahydronaphthyl, fluorenyl and the like.

The term "aromatic heterocyclyl" means an aromatic cyclyl, which is monocyclic or polycyclic having two or more rings, containing one or more of heteroatom(s) selected independently from O, S and N.

Examples of aromatic heterocyclyl, which is polycyclic having two or more rings, include a fused ring group wherein an aromatic heterocyclyl, which is monocyclic or polycyclic having two or more rings, is fused with a ring of the above "aromatic carbocyclyl".

The aromatic heterocyclyl, which is monocyclic, is preferably a 5- to 8-membered and more preferably 5- to 6-membered ring. Examples include pyrrolyl, imidazolyl, pyrazolyl, pyridyl, pyridazinyl, pyrimidinyl, pyrazinyl, triazolyl, triazinyl, tetrazolyl, furyl, thienyl, isoxazolyl, oxazolyl, oxadiazolyl, isothiazolyl, thiazolyl, thiadiazolyl and the like.

Examples of aromatic heterocyclyl, which is bicyclic, include indolyl, isoindolyl, indazolyl, indolizinyl, quinolinyl, isoquinolinyl, cinnolinyl, phthalazinyl, quinazolinyl, naphthyridinyl, quinoxalinyl, purinyl, pteridinyl, benzimidazolyl, benzisoxazolyl, benzoxazolyl, benzoxadiazolyl, benzisothiazolyl, benzothiazolyl, benzothiadiazolyl, benzofuryl, isobenzofuryl, benzothienyl, benzotriazolyl, imidazopyridyl, triazolopyridyl, imidazothiazolyl, pyrazinopyridazinyl, oxazolopyridyl, thiazolopyridyl and the like.

Examples of aromatic heterocyclyl, which is polycyclic having three or more rings, include carbazolyl, acridinyl, xanthenyl, phenothiazinyl, phenoxathiinyl, phenoxazinyl, dibenzofuryl and the like.

The term "non-aromatic heterocyclyl" means a non-aromatic cyclyl, which is monocyclic or polycyclic having two or more rings, containing one or more heteroatom(s) selected independently from O, S and N.

Examples of non-aromatic heterocyclyl, which is polycyclic having two or more rings, include a fused ring group wherein a non-aromatic heterocycle, which is monocyclic or polycyclic having two or more rings, is fused with a ring of the above "aromatic carbocyclyl", "non-aromatic carbocyclyl" and/or "aromatic heterocyclyl".

In addition, examples of the "non-aromatic heterocyclyl" also include a group having a bridge or a group to form a spiro ring as follows:

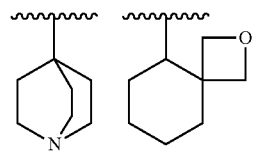

The non-aromatic heterocyclyl, which is monocyclic, is preferably a 3- to 8-membered and more preferably 5- to 6-membered ring. Examples include dioxanyl, thiiranyl, oxiranyl, oxetanyl, oxathiolanyl, azetidinyl, thianyl, thiazolidinyl, pyrrolidinyl, pyrrolinyl, imidazolidinyl, imidazolinyl, pyrazolidinyl, pyrazolinyl, piperidyl, piperazinyl, morpholinyl, morpholino, thiomorpholinyl, thiomorpholino, dihydropyridyl, tetrahydropyridyl, tetrahydrofuryl, tetrahydropyranyl, dihydrothiazolyl, tetrahydrothiazolyl, tetrahydroisothiazolyl, dihydrooxazinyl, hexahydroazepinyl, tetrahydrodiazepinyl, tetrahydropyridazinyl, hexahydropyrimidinyl, dioxolanyl, dioxazinyl, aziridinyl, dioxolinyl, oxepanyl, thiolanyl, thiinyl, thiazinyl and the like.

Examples of non-aromatic heterocyclyl, which is polycyclic having two or more rings, include indolinyl, isoindolinyl, chromanyl, isochromanyl and the like.

The term "alkyloxy" means a group wherein the above "alkyl" is bonded to an oxygen atom. Examples include methyloxy, ethyloxy, n-propyloxy, isopropyloxy, n-butyloxy, tert-butyloxy, isobutyloxy, sec-butyloxy, pentyloxy, isopentyloxy, hexyloxy and the like.

A preferred embodiment of "alkyloxy" is methyloxy, ethyloxy, n-propyloxy, isopropyloxy or tert-butyloxy.

The term "haloalkyl" means a group wherein one or more "halogen" described above is bonded to the above "alkyl". Examples include monofluoromethyl, monofluoroethyl, monofluoropropyl, 2,2,3,3,3-pentafluoropropyl, monochloromethyl, trifluoromethyl, trichloromethyl, 2,2,2-trifluoroethyl, 2,2,2-trichloroethyl, 1,2-dibromoethyl, 1,1,1-trifluoropropan-2-yl and the like.

A preferred embodiment of "haloalkyl" is trifluoromethyl or trichloromethyl.

The term "alkylamino" includes monoalkylamino and dialkylamino.

The term "monoalkylamino" means a group wherein a hydrogen atom attached to a nitrogen atom of an amino group is replaced with the above "alkyl". Examples include methylamino, ethylamino, isopropylamino and the like. Preferably, it is methylamino or ethylamino.

The term "dialkylamino" means a group wherein two hydrogen atoms attached to a nitrogen atom of an amino group are replaced with two "alkyl" described above. These two alkyl groups may be the same or different. Examples include dimethylamino, diethylamino, N,N-diisopropylamino, N-methyl-N-ethylamino, N-isopropyl-N-ethylamino and the like. Preferably, it is dimethylamino or diethylamino.

The term "alkylcarbonylamino" means a group wherein one or two hydrogen atoms attached to a nitrogen atom of an amino group are replaced with one or two alkylcarbonyl. The two alkylcarbonyl groups may be the same or different. Examples include methylcarbonylamino, ethylcarbonylamino, propylcarbonylamino, isopropylcarbonylamino, tert-butylcarbonylamino, isobutylcarbonylamino, sec-butylcarbonylamino, dimethylcarbonylamino, diethylcarbonylamino, N,N-diisopropylcarbonylamino and the like.

A preferred embodiment of "alkylcarbonylamino" is methylcarbonylamino and ethylcarbonylamino.

The term "alkenylcarbonylamino" means a group wherein one or two hydrogen atoms attached to a nitrogen atom of an amino group are replaced with one or two alkenylcarbonyl. The two alkenylcarbonyl groups may be the same or different. Examples include vinylcarbonylamino, propenylcarbonylamino and the like.

The term "alkynylcarbonylamino" means a group wherein one or two hydrogen atoms attached to a nitrogen atom of an amino group are replaced with one or two alkynylcarbonyl. The two alkynylcarbonyl groups may be the same or different. Examples include ethynylcarbonylamino, propynylcarbonylamino and the like.

The term "alkylcarbamoyl" means a group wherein one or two hydrogen atoms attached to a nitrogen atom of a carbamoyl group are replaced with one or two "alkyl" described above. These two alkyl groups may be the same or different. Examples include methylcarbamoyl, ethylcarbamoyl, dimethylcarbamoyl, diethylcarbamoyl and the like.

The term "alkenylcarbamoyl" means a group wherein one or two hydrogen atoms attached to a nitrogen atom of a carbamoyl group are replaced with one or two "alkenyl" described above. These two alkenyl groups may be the same or different. Examples include vinylcarbamoyl, propenylcarbamoyl and the like.

The term "alkynylcarbamoyl" means a group wherein one or two hydrogen atoms attached to a nitrogen atom of a carbamoyl group are replaced with one or two "alkynyl" described above. These two alkynyl groups may be the same or different. Examples include ethynylcarbamoyl, propynylcarbamoyl and the like.

Examples of the substituents for "substituted or unsubstituted alkyl", "substituted or unsubstituted alkenyl", "substituted or unsubstituted alkynyl", "substituted or unsubstituted alkylcarbonylamino", "substituted or unsubstituted alkenylcarbonylamino", "substituted or unsubstituted alkynylcarbonylamino", "substituted or unsubstituted alkylcarbamoyl", "substituted or unsubstituted alkenylcarbamoyl" and "substituted or unsubstituted alkynylcarbamoyl" include the following substituents. A carbon atom(s) at any position(s) may be bonded to one or more group(s) selected from the following substituents.

Substituents: halogen, hydroxy, carboxy, amino, imino, hydroxyamino, hydroxyimino, formyl, formyloxy, carbamoyl, sulfamoyl, sulfanyl, sulfino, sulfo, thioformyl, thiocarboxy, dithiocarboxy, thiocarbamoyl, cyano, nitro, nitroso, azide, hydrazino, ureide, amidino, guanidino, trialkylsilyl, alkyloxy, alkenyloxy, alkynyloxy, haloalkyloxy, alkylcarbonyl, alkenylcarbonyl, alkynylcarbonyl, monoalkylamino, dialkylamino, alkylsulfonyl, alkenylsulfonyl, alkynylsulfonyl, monoalkylcarbonylamino, dialkylcarbonylamino, monoalkylsulfonylamino, dialkylsulfonylamino, alkylimino, alkenylimino, alkynylimino, alkylcarbonylimino, alkenylcarbonylimino, alkynylcarbonylimino, alkyloxyimino, alkenyloxyimino, alkynyloxyimino, alkylcarbonyloxy, alkenylcarbonyloxy, alkynylcarbonyloxy, alkyloxycarbonyl, alkenyloxycarbonyl, alkynyloxycarbonyl, alkylsulfanyl, alkenylsulfanyl, alkynylsulfanyl, alkylsulfinyl, alkenylsulfinyl, alkynylsulfinyl, monoalkylcarbamoyl, dialkylcarbamoyl, monoalkylsulfamoyl, dialkylsulfamoyl, aromatic carbocyclyl, non-aromatic carbocyclyl, aromatic heterocyclyl, non-aromatic heterocyclyl, aromatic carbocyclyloxy, non-aromatic carbocyclyloxy, aromatic heterocyclyloxy, non-aromatic heterocyclyloxy, aromatic carbocyclylcarbonyl, non-aromatic carbocyclylcarbonyl, aromatic heterocyclylcarbonyl, non-aromatic heterocyclylcarbonyl, aromatic carbocyclyloxycarbonyl, non-aromatic carbocyclyloxycarbonyl, aromatic heterocyclyloxycarbonyl, non-aromatic heterocyclyloxycarbonyl, aromatic carbocyclylalkyloxy, non-aromatic carbocyclylalkyloxy, aromatic heterocyclylalkyloxy, non-aromatic heterocyclylalkyloxy, aromatic carbocyclylalkyloxycarbonyl, non-aromatic carbocyclylalkyloxycarbonyl, aromatic heterocyclylalkyloxycarbonyl, non-aromatic heterocyclylalkyloxycarbonyl, aromatic carbocyclylalkylamino, non-aromatic carbocyclylalkylamino, aromatic heterocyclylalkylamino, non-aromatic heterocyclylalkylamino, aromatic carbocyclylsulfanyl, non-aromatic carbocyclylsulfanyl, aromatic heterocyclylsulfanyl, non-aromatic heterocyclylsulfanyl, non-aromatic carbocyclylsulfonyl, aromatic carbocyclylsulfonyl, aromatic heterocyclylsulfonyl and non-aromatic heterocyclylsulfonyl.

Examples of the substituents on the ring of "aromatic carbocycle" in "substituted or unsubstituted aromatic carbocyclyl (aryl)" include the following substituents. An atom(s) at any position(s) on the ring may be bonded to one or more group(s) selected from the following substituents.

Substituents: halogen, hydroxy, carboxy, amino, imino, hydroxyamino, hydroxyimino, formyl, formyloxy, carbamoyl, sulfamoyl, sulfanyl, sulfino, sulfo, thioformyl, thiocarboxy, dithiocarboxy, thiocarbamoyl, cyano, nitro, nitroso, azide, hydrazino, ureide, amidino, guanidino, trialkylsilyl, alkyl, alkenyl, alkynyl, haloalkyl, alkyloxy, alkenyloxy, alkynyloxy, haloalkyloxy, alkyloxyalkyl, alkyloxyalkyloxy, alkylcarbonyl, alkenylcarbonyl, alkynylcarbonyl, monoalkylamino, dialkylamino, alkylsulfonyl, alkenylsulfonyl, alkynylsulfonyl, monoalkylcarbonylamino, dialkylcarbonylamino, monoalkylsulfonylamino, dialkylsulfonylamino, alkylimino, alkenylimino, alkynylimino, alkylcarbonylimino, alkenylcarbonylimino, alkynylcarbonylimino, alkyloxyimino, alkenyloxyimino, alkynyloxyimino, alkylcarbonyloxy, alkenylcarbonyloxy, alkynylcarbonyloxy, alkyloxycarbonyl, alkenyloxycarbonyl, alkynyloxycarbonyl, alkylsulfanyl, alkenylsulfanyl, alkynylsulfanyl, alkylsulfinyl, alkenylsulfinyl, alkynylsulfinyl, monoalkylcarbamoyl, dialkylcarbamoyl, monoalkylsulfamoyl, dialkylsulfamoyl, aromatic carbocyclyl, non-aromatic carbocyclyl, aromatic heterocyclyl, non-aromatic heterocyclyl, aromatic carbocyclyloxy, non-aromatic carbocyclyloxy, aromatic heterocyclyloxy, non-aromatic heterocyclyloxy, aromatic carbocyclylcarbonyl, non-aromatic carbocyclylcarbonyl, aromatic heterocyclylcarbonyl, non-aromatic heterocyclylcarbonyl, aromatic carbocyclyloxycarbonyl, non-aromatic carbocyclyloxycarbonyl, aromatic heterocyclyloxycarbonyl, non-aromatic heterocyclyloxycarbonyl, aromatic carbocyclylalkyl, non-aromatic carbocyclylalkyl, aromatic heterocyclylalkyl, non-aromatic heterocyclylalkyl, aromatic carbocyclylalkyloxy, non-aromatic carbocyclylalkyloxy, aromatic heterocyclylalkyloxy, non-aromatic heterocyclylalkyloxy, aromatic carbocyclylalkyloxycarbonyl, non-aromatic carbocyclylalkyloxycarbonyl, aromatic heterocyclylalkyloxycarbonyl, non-aromatic heterocyclylalkyloxycarbonyl, aromatic carbocyclylalkyloxyalkyl, non-aromatic carbocyclylalkyloxyalkyl, aromatic heterocyclylalkyloxyalkyl, non-aromatic heterocyclylalkyloxyalkyl, aromatic carbocyclylalkylamino, non-aromatic carbocyclylalkylamino, aromatic heterocyclylalkylamino, non-aromatic heterocyclylalkylamino, aromatic carbocyclylsulfanyl, non-aromatic carbocyclylsulfanyl, aromatic heterocyclylsulfanyl, non-aromatic heterocyclylsulfanyl, non-aromatic carbocyclylsulfonyl, aromatic carbocyclylsulfonyl, aromatic heterocyclylsulfonyl and non-aromatic heterocyclylsulfonyl.

Preferred embodiments of a compound of formula (I) of the present invention are disclosed below.

$Y^1$ is $CR^6$ or N.

$Y^2$ is $CR^7$ or N.

$Y^3$ is $CR^8$ or N.

$R^6$, $R^7$ and $R^8$ are each independently, a hydrogen atom, halogen, cyano, substituted or unsubstituted alkyl, substituted or unsubstituted alkenyl, substituted or unsubstituted alkynyl, substituted or unsubstituted amino, substituted or unsubstituted alkoxy, substituted or unsubstituted alkylcarbonylamino, substituted or unsubstituted alkenylcarbonylamino, substituted or unsubstituted alkynylcarbonylamino, substituted or unsubstituted alkylcarbamoyl, substituted or unsubstituted alkenylcarbamoyl, or substituted or unsubstituted alkynylcarbamoyl. Preferably, it is a hydrogen atom, or substituted or unsubstituted alkyl.

Concretely, a group of the formula:

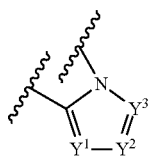

is a group of the formula,

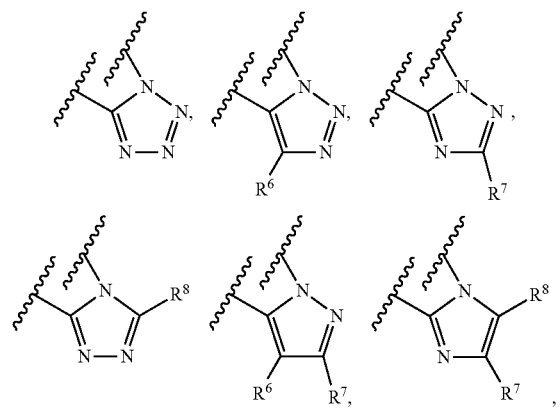

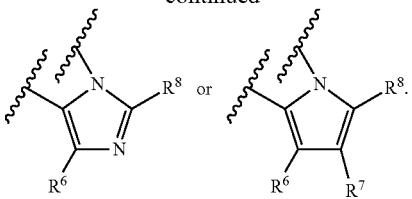

Preferably, a group of the formula:

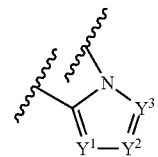

is a group of the formula:

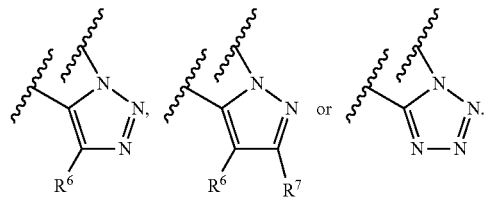

Bx is a nucleic acid base moiety. More preferably, it is substituted or unsubstituted purin-9-yl, or substituted or unsubstituted 2-oxo-pyrimidin-1-yl.

$Z^1$ is each independently, a hydrogen atom, a hydroxyl protecting group or a reactive phosphorus group. Preferably, it is a hydrogen atom or a hydroxyl protecting group. More preferably, it is a hydrogen atom, acetyl, t-butyl, t-butoxymethyl, methoxymethyl, tetrahydropyranyl, 1-ethoxyethyl, 1-(2-chloroethoxy)-ethyl, 2-trimethylsilylethyl, p-chlorophenyl, 2,4-dinitrophenyl, benzyl, benzoyl, p-phenylbenzoyl, 2,6-dichlorobenzyl, levulinoyl, diphenylmethyl, p-nitrobenzyl, trimethylsilyl, triethylsilyl, t-butyldimethylsilyl, t-butyldiphenylsilyl, triphenylsilyl, triisopropylsilyl, benzoyl formate, chloroacetyl, trichioroacetyl, trifluoroacetyl, pivaloyl, isobutyryl, 9-fluorenylmethyloxycarbonyl, methansulfonyl, p-toluenesulfonyl, trifluoromethanesulfonyl, triphenylmethyl (trityl), monomethoxytrityl, dimethoxytrityl (DMTr), trimethoxytrityl, 9-phenylxanthine-9-yl (Pixyl) or 9-(p-methoxyphenyl)xanthin-9-yl (MOX). Especially preferably, it is a hydrogen atom, benzyl, triethylsilyl, t-butyldimethylsilyl, t-butyldiphenylsilyl, triisopropylsilyl, trityl, monomethoxytrityl, dimethoxytrityl, trimethoxytrityl or the like.

$Z^2$ is each independently, a hydrogen atom, a hydroxyl protecting group or a reactive phosphorus group. Preferably, it is a hydrogen atom or a reactive phosphorus group. More preferably, it is a hydrogen atom, diisopropylcyanoethoxy phosphoramidite or H-phosphonate.

$R^1$ and $R^2$ are each independently, a hydrogen atom, halogen, cyano, substituted or unsubstituted alkyl, substituted or unsubstituted alkenyl, or substituted or unsubstituted alkynyl. Preferably, it is a hydrogen atom or alkyl.

$R^3$ are each independently, a hydrogen atom, halogen, cyano, substituted or unsubstituted alkyl, substituted or unsubstituted alkenyl, or substituted or unsubstituted alkynyl. Preferably, it is a hydrogen atom, halogen, cyano or alkyl.

$R^4$ are each independently, a hydrogen atom, halogen, cyano, substituted or unsubstituted alkyl, substituted or unsubstituted alkenyl, or substituted or unsubstituted alkynyl. Preferably, it is a hydrogen atom, halogen, cyano or alkyl.

$R^5$ is a hydrogen atom, halogen, cyano, substituted or unsubstituted alkyl, substituted or unsubstituted alkenyl, or substituted or unsubstituted alkynyl. Preferably, it is a hydrogen atom, halogen, cyano or alkyl.

n is an integer of 0 to 3. Preferably, it is 0 or 1.

The compounds of formula (I) are not limited to specific isomers but include all possible isomers (e.g., keto-enol isomers, imine-enamine isomers, diastereoisomers, enantiomers, rotamers or the like), racemates or mixtures thereof.

One or more hydrogen, carbon and/or other atoms in the compounds of formula (I) may be replaced with isotopes of hydrogen, carbon and/or other atoms respectively. Examples of the isotopes include hydrogen, carbon, nitrogen, oxygen, phosphorus, sulfur, fluorine, iodine and chlorine, such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$, $^{123}I$ and $^{36}Cl$ respectively. The compounds of formula (I) include compounds replaced with these isotopes. The compounds replaced with the above isotopes are useful as pharmaceuticals and include all of radiolabeled compounds of the compound of formula (I). A "method of radiolabeling" in the manufacture of the "radiolabeled compounds" is encompassed by the present invention, and the "radiolabeled compounds" are useful for studies on metabolized drug pharmacokinetics, studies on binding assay and/or diagnostic tools.

A radiolabeled compound of formula (I) can be prepared using well-known methods in this field of the invention. For example, a tritium-labeled compound of formula (I) can be prepared by introducing a tritium to a compound of formula (I), through a catalytic dehalogenation reaction using a tritium. This method comprises reacting with an appropriately-halogenated precursor of the compound of formula (I) with tritium gas in the presence of an appropriate catalyst, such as Pd/C, and in the presence or absent of a base. The other appropriate method of preparing a tritium-labeled compound can be referred to "Isotopes in the Physical and Biomedical Sciences, Vol. 1, Labeled Compounds (Part A), Chapter 6 (1987)". A $^{14}C$-labeled compound can be prepared by using a raw material having $^{14}C$ carbon.

The present invention encompasses preparable salts of the compounds of formula (I). The salts include, for example, alkaline metal salts such as sodium salts, potassium salts, lithium salts and the like; alkaline earth metal salts such as calcium salts, magnesium salts and the like; metal salts such as aluminum salts, iron salts, zinc salts, copper salts, nickel salts, cobalt salts and the like; ammonium salt; amine salts such as t-octylamine salts, dibenzylamine salts, morpholine salts, glucosamine salts, phenylglycine alkylester salts, ethylenediamine salts, N-methylglucamine salts, guanidine salts, diethylamine salts, triethylamine salts, dicyclohexylamine salts, N,N'-dibenzylethylenediamine salts, chloroprocaine salts, procaine salts, diethanolamine salts, N-benzyl-phenethylamine salts, piperazine salts, tetramethylammonium salts, Tris(hydroxymethyl)aminomethane salts and the like; inorganic acid salts such as halide acid salts (hydrofluoride, hydrochloride, hydrobromide, hydriodide and the like), nitrates, perchlorates, sulfates, phosphates and the like; alkanesulfonates such as methanesulfonates, trifluoromethanesulfonates, ethanesulfonates and the like; arylsulfonates salts such as benzenesulfonates, p-toluenesulfonates and the like; organic acid salts such as acetates, malates, fumarates, succinates, citrates, tartrates, oxalates, maleates and the like; amino acid salts such as glycine salts, lysine salts, arginine salts, ornithine salts, glutamates, aspartates and the like; etc. These salts can be formed by the usual methods.

The compounds of formula (I) of the present invention or salts thereof may form solvates (e.g., hydrates or the like) and/or crystal polymorphs. The present invention encompasses those various solvates and crystal polymorphs. "Solvates" may be those wherein any numbers of solvent molecules (e.g., water molecules or the like) are coordinated with the compounds of formula (I). When the compounds of formula (I) or pharmaceutically acceptable salts thereof are allowed to stand in the atmosphere, the compounds may absorb water, resulting in attachment of adsorbed water or formation of hydrates. Recrystallization of the compounds of formula (I) or pharmaceutically acceptable salts thereof may produce crystal polymorphs.

Compounds of formula (I) of the present invention can be synthesized based on the publicly known methods in this field. For example, they can be produced by the general synthetic methods described below. Additionally, the methods for extraction, purification and the like may be carried out by using the usual methods for the experiments of organic chemistry.

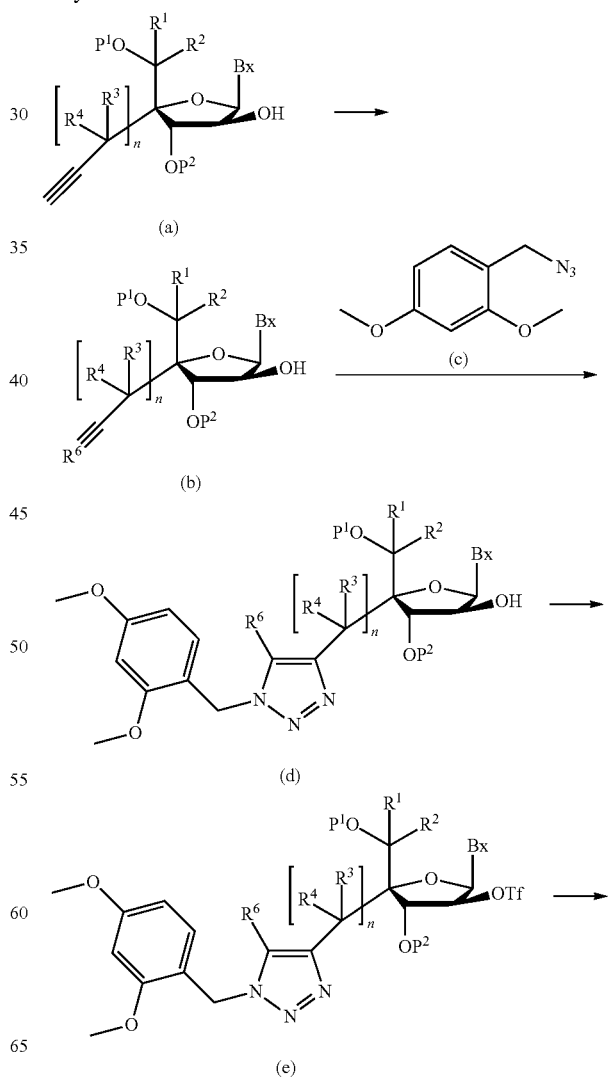

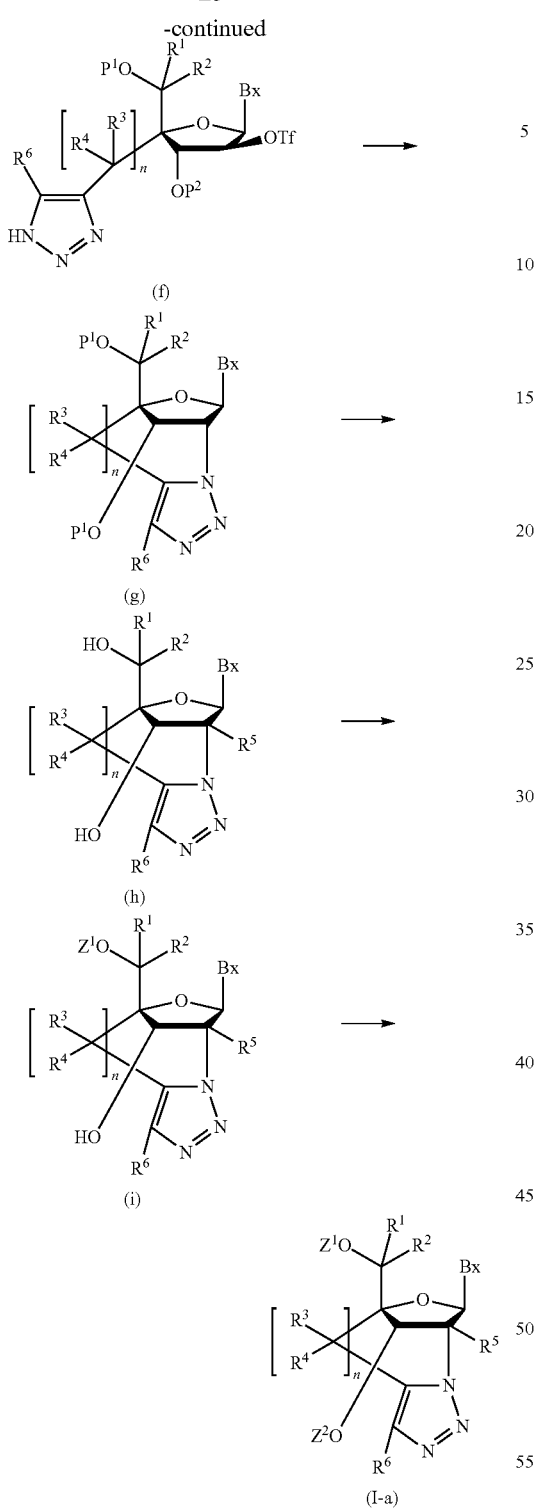

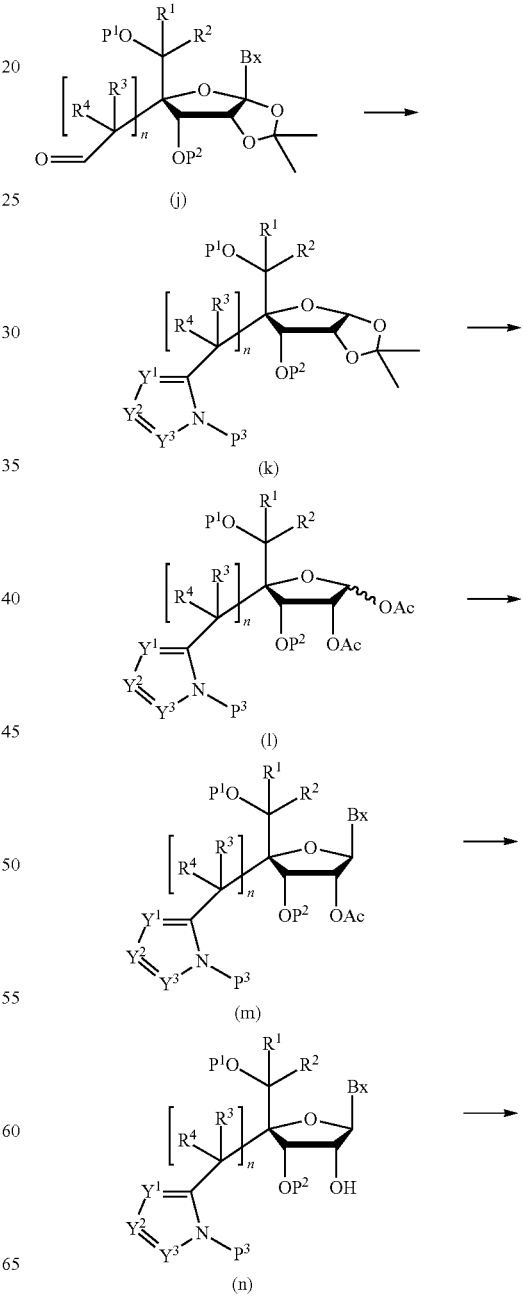

As-needed $R^6$ is introduced into compound (a) to give compound (b). Compound (b) and compound (c) are reacted under the presence of base and catalyst to give compound (d). After converting into compound (e) by changing the hydroxyl group at 2'-position to triflate, the protective group of nitrogen atom is removed to give compound (f). The resultant compound (f) is treated with base to give compound (g). Subsequently, the protective groups of the hydroxyl groups at 3'-position and 5'-position are removed, and a substituent is introduced into $R^5$ as needed, to give compound (h). A protective group (especially, a trityl group optionally substituted by a methoxy group) is introduced into the hydroxyl group at 5'-position to give compound (i). A reactive phosphorus group (especially, diisopropylcyanoethoxy phosphoramidite) is introduced into the hydroxyl group at 3'-position to give compound (I-a).

wherein $P^1$ and $P^2$ are each independently, a hydroxyl protecting group, preferably benzyl, naphthyl, t-butyldimethylsilyl, t-butyldiphenylsilyl or benzoyl. $Z^1$ is a hydroxyl protecting group, preferably t-butyldimethylsilyl, t-butyldiphenylsilyl, triisopropylsilyl, trityl, monomethoxytrityl, dimethoxytrityl or trimethoxytrityl. $Z^2$ is a reactive phosphorus group, preferably diisopropylcyanoethoxy phosphoramidite or H-phosphonate. Each of the other symbols has the same meaning as those of a compound of the formula (I).

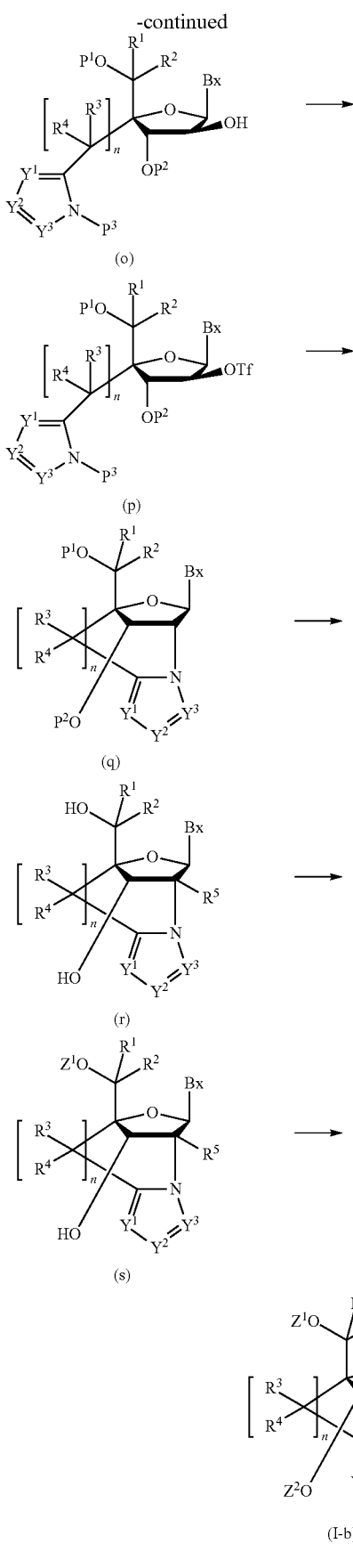

wherein $P^1$ and $P^2$ are each independently, a hydroxyl protecting group, preferably benzyl, naphthyl, t-butyldimethylsilyl, t-butyldiphenylsilyl or benzoyl. $P^3$ is a protective group for a nitrogen atom, preferably benzyl, naphthyl, pivaloyl or methylpivalate. $Z^1$ is a hydroxyl protecting group, preferably t-butyldimethylsilyl, t-butyldiphenylsilyl, triisopropylsilyl, trityl, monomethoxytrityl, dimethoxytrityl or trimethoxytrityl. $Z^2$ is a reactive phosphorus group, preferably diisopropylcyanoethoxy phosphoramidite or H-phosphonate. Each of the symbols of the formula has the same meaning as those of a compound of the formula (I).

Heterocycle having as-needed substituent(s) is introduced into compound (j) to give compound (k). After deprotecting acetonide to give compound (l), a nucleic acid base moiety is introduced to give compound (m). After removing the acetyl group, the steric structure of the hydroxyl group at 2'-position is inverted to give compound (o). After converting into compound (p) by changing the hydroxyl group to triflate, the protective group of a nitrogen atom is removed, and the resultant compound is treated with base to give compound (q). Subsequently, the protective groups of the hydroxyl groups at 3'-position and 5'-position are removed, and a substituent is introduced into $R^5$ as needed, to give compound (r). A protective group (especially, a trityl group optionally substituted by a methoxy group) is introduced into the hydroxyl group at 5'-position to give compound (s). A reactive phosphorus group (especially, diisopropylcyanoethoxy phosphoramidite) is introduced into the hydroxyl group at 3'-position to give compound (I-b).

In the above steps, the following intermediates are useful.

A compound of the formula:

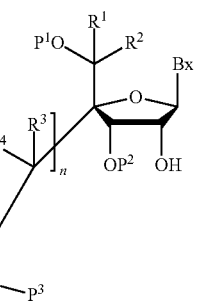

wherein $P^1$ and $P^2$ are each independently, a hydroxyl protecting group, preferably benzyl, naphthyl, t-butyldimethylsilyl, t-butyldiphenylsilyl or benzoyl. $P^3$ is a protective group for a nitrogen atom, preferably benzyl, naphthyl, pivaloyl or methylpivalate. Each of the symbols of the formula has the same meaning as those of a compound of the formula (I).

The nucleoside of the present invention means a compound of compound (I) wherein $Z^1$ and $Z^2$ is a hydrogen atom.

The nucleotide of the present invention means a compound of compound (I) wherein $Z^2$ is a reactive phosphorus group.

The present invention encompasses a following oligonucleotide prepared with a compound of formula (I), or a pharmaceutically acceptable salt thereof.

An oligonucleotide comprising one or more nucleoside structure of formula (II) or a pharmaceutically acceptable salt thereof

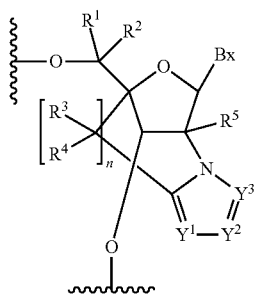

(II)

wherein
Y$^1$ is CR$^6$ or N,
Y$^2$ is CR$^7$ or N,
Y$^3$ is CR$^8$ or N,
R$^6$, R$^7$ and R$^8$ are each independently, a hydrogen atom, halogen, cyano, substituted or unsubstituted alkyl, substituted or unsubstituted alkenyl, substituted or unsubstituted alkynyl, substituted or unsubstituted amino, substituted or unsubstituted alkoxy, substituted or unsubstituted alkylcarbonylamino, substituted or unsubstituted alkenylcarbonylamino, substituted or unsubstituted alkynylcarbonylamino, substituted or unsubstituted alkylcarbamoyl, substituted or unsubstituted alkenylcarbamoyl, or substituted or unsubstituted alkynylcarbamoyl,
Bx is a nucleic acid base moiety,
R$^1$ and R$^2$ are each independently, a hydrogen atom, halogen, cyano, substituted or unsubstituted alkyl, substituted or unsubstituted alkenyl, or substituted or unsubstituted alkynyl,
R$^3$ are each independently, a hydrogen atom, halogen, cyano, substituted or unsubstituted alkyl, substituted or unsubstituted alkenyl, or substituted or unsubstituted alkynyl,
R$^4$ are each independently, a hydrogen atom, halogen, cyano, substituted or unsubstituted alkyl, substituted or unsubstituted alkenyl, or substituted or unsubstituted alkynyl,
R$^5$ is a hydrogen atom, halogen, cyano, substituted or unsubstituted alkyl, substituted or unsubstituted alkenyl, or substituted or unsubstituted alkynyl, and
n is an integer of 0 to 3.

Each of the symbols of the formula has the same meaning as those of a compound of the formula (I).

The oligonucleotide of the present invention is an oligonucleotide whose length is 2 to 50 bases, and preferably 8 to 30 bases, and which comprises at least one nucleoside structure of formula (II) at any position(s). The position and number of the nucleoside structures are not limited to the specific position and number and may be appropriately selected depending on the purposes. For example, the nucleoside structure of formula (II) can be comprised at the 3'-terminus or 5'-terminus of the oligonucleotide. When it is comprised at the 3'-terminus, the structure is as below.

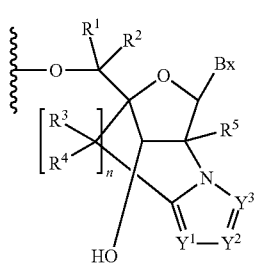

(II)

wherein each of the symbols has the same meaning as those of a compound of the formula (I).

When it is comprised at the 5'-terminus, the structure is as below.

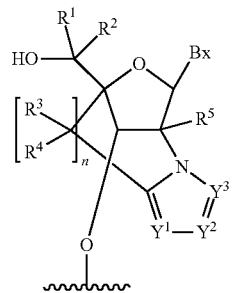

(II)

wherein each of the symbols has the same meaning as those of a compound of the formula (I).

The 3'-terminus and/or 5'-terminus of an oligonucleotide of the present invention can be modified. The modified groups publicly known in this field can be used to allow tracking of the oligonucleotide, to improve pharmacokinetics or pharmacodynamics of the oligonucleotide, or to enhance stability or binding affinity of the oligonucleotide. Examples include protective groups for a hydroxyl group, reporter molecule, cholesterol, phospholipid, dye, fluorescent molecule and the like.

Alternatively, the 3'-terminus and/or 5'-terminus of an oligonucleotide of the present invention can comprise phosphate ester moieties. The term "phosphate ester moiety" means a phosphate group at the terminus comprising phosphoester or modified phosphoester. The phosphate ester moiety can be located at either terminus, but preferably it is a 5'-terminus nucleoside. Concretely, it is a group of the formula: —O—P(=O)(OH)OH or a modified group thereof. In other words, one or more O or OH is optionally substituted by H, O, OR$^X$, S, N(R$^X$), or alkyl wherein R$^X$ is H, an amino protecting group, or substituted or unsubstituted alkyl. A group at the 5'- and/or 3'-terminus can comprise each independently substituted or unsubstituted 1 to 3 phosphate ester moiety.

As long as an oligonucleotide of the present invention comprise at least one nucleoside structure of formula (II), the other parts can be same with natural nucleic acids or have nucleotide modifications publicly known in this field.

Examples of a phosphate moiety of an oligonucleotide of the present invention include phosphodiester linkage comprised in natural nucleic acids, S-oligo (phosphorothioate), M-oligo (methylphosphonate), borano phosphate and the like.

A base moiety except for nucleoside structures of formula (II) in an oligonucleotide of the present invention can be any nucleic acid base defined as the above "Bx".

Examples of a sugar moiety except for nucleoside structures of formula (II) in an oligonucleotide of the present invention are natural ribose or deoxyribose, ribose or deoxyribose with the publicly known modification, and the like. Examples of the publicly known modifications are modifications by 2'-O—CH$_2$—CH$_2$—O—CH$_3$ (2'MOE), 4'-CH$_2$—O-2' (LNA, Locked nucleic acid), AmNA (amideBNA) (Bridged nucleic acid, WO2011/052436) and the like.

Additionally, internucleoside linkages comprised in an oligonucleotide of the present invention can be linkages not having a phosphorus atom as long as they are publicly known in this field. They include alkyl, non-aromatic carbocycle, non-aromatic carbocycle substituted by haloalkyl or halogen and the like, but are not limited to them. Examples include siloxane, sulfide, sulfoxide, sulfone, acetyl, acetyl formate, thioacetyl formate, methyleneacetyl formate, thioacetyl formate, alkenyl, sulfamate, methyleneimino, methylenehydrazino, sulfonate, sulfonamide and amide.

The oligonucleotides of the present invention are not limited to specific isomers but include all possible isomers (e.g., keto-enol isomers, imine-enamine isomers, diastereoisomers, enantiomers, rotamers or the like), racemates or mixtures thereof.

One or more hydrogen, carbon and/or other atoms in the oligonucleotides of the present invention may be replaced with isotopes of hydrogen, carbon and/or other atoms respectively. Examples of the isotopes include hydrogen, carbon, nitrogen, oxygen, phosphorus, sulfur, fluorine, iodine and chlorine, such as $^2$H, $^3$H, $^{11}$C, $^{13}$C, $^{14}$C, $^{15}$N, $^{18}$O, $^{17}$O, $^{31}$P, $^{32}$P, $^{35}$S $^{18}$F, $^{123}$I and $^{36}$Cl respectively. The oligonucleotides of the present invention include oligonucleotides replaced with these isotopes. The oligonucleotides replaced with the above isotopes are useful as pharmaceuticals and include all of radiolabeled compounds of the oligonucleotides of the present invention. A "method of radiolabeling" in the manufacture of the "radiolabeled compounds" is encompassed by the present invention, and the "radiolabeled compounds" are useful for studies on metabolized drug pharmacokinetics, studies on binding assay and/or diagnostic tools.

A radiolabeled compound of the oligonucleotides of the present invention can be prepared using well-known methods in this field of the invention. For example, a tritium-labeled oligonucleotide of the present invention can be prepared by introducing a tritium to an oligonucleotide of the present invention, through a catalytic dehalogenation reaction using a tritium. This method comprises reacting with an appropriately-halogenated precursor of the oligonucleotide of the present invention with tritium gas in the presence of an appropriate catalyst, such as Pd/C, and in the presence or absent of a base. The other appropriate method of preparing a tritium-labeled compound can be referred to "Isotopes in the Physical and Biomedical Sciences, Vol. 1, Labeled Compounds (Part A), Chapter 6 (1987)". A $^{14}$C-labeled compound can be prepared by using a raw material having $^{14}$C carbon.

The present invention encompasses pharmaceutically acceptable salts of the oligonucleotides of the present invention. The salts include, for example, alkaline metal salts such as sodium salts, potassium salts, lithium salts and the like; alkaline earth metal salts such as calcium salts, magnesium salts and the like; metal salts such as aluminum salts, iron salts, zinc salts, copper salts, nickel salts, cobalt salts and the like; ammonium salt; amine salts such as t-octylamine salts, dibenzylamine salts, morpholine salts, glucosamine salts, phenylglycine alkylester salts, ethylenediamine salts, N-methylglucamine salts, guanidine salts, diethylamine salts, triethylamine salts, dicyclohexylamine salts, N,N'-dibenzylethylenediamine salts, chloroprocaine salts, procaine salts, diethanolamine salts, N-benzyl-phenethylamine salts, piperazine salts, tetramethylammonium salts, Tris(hydroxymethyl)aminomethane salts and the like; inorganic acid salts such as halide acid salts (hydrofluoride, hydrochloride, hydrobromide, hydriodide and the like), nitrates, perchlorates, sulfates, phosphates and the like; alkanesulfonates such as methanesulfonates, trifluoromethanesulfonates and ethanesulfonates; arylsulfonates salts such as benzenesulfonates, p-toluenesulfonates and the like; organic acid salts such as acetates, malates, fumarates, succinates, citrates, tartrates, oxalates, maleates and the like; amino acid salts such as glycine salts, lysine salts, arginine salts, ornithine salts, glutamates, aspartates and the like; etc. These salts can be formed by the usual methods.

The oligonucleotides of the present invention or pharmaceutically acceptable salts thereof may form solvates (e.g., hydrates or the like) and/or crystal polymorphs. The present invention encompasses those various solvates and crystal polymorphs. "Solvates" may be those wherein any numbers of solvent molecules (e.g., water molecules or the like) are coordinated with the oligonucleotides of the present invention. When the oligonucleotides of the present invention or pharmaceutically acceptable salts thereof are allowed to stand in the atmosphere, the compounds may absorb water, resulting in attachment of adsorbed water or formation of hydrates. Recrystallization of the oligonucleotides of the present invention or pharmaceutically acceptable salts thereof may produce crystal polymorphs.

The oligonucleotides or pharmaceutically acceptable salts thereof of the present invention may form prodrugs. The present invention also encompasses such various prodrugs. Prodrugs are derivatives of the compounds of the present invention with a chemically or metabolically degradable group(s), and compounds that are converted to the pharmaceutically active oligonucleotide of the present invention through solvolysis or under physiological conditions in vivo. Prodrugs include compounds that are converted to the oligonucleotides of the present invention through enzymatic oxidation, reduction, hydrolysis or the like under physiological conditions in vivo, compounds that are converted to the oligonucleotides of the present invention through hydrolysis by gastric acid etc., and the like. Methods for selecting and preparing suitable prodrug derivatives are described in, for example, "Design of Prodrugs, Elsevier, Amsrdam, 1985". Prodrugs themselves may have some activity.

When the oligonucleotides or pharmaceutically acceptable salts thereof of the present invention have hydroxyl group(s), the prodrugs include acyloxy derivatives and sulfonyloxy derivatives that are prepared by, for example, reacting compounds having hydroxyl group(s) with suitable acyl halide, suitable acid anhydride, suitable sulfonyl chloride, suitable sulfonyl anhydride or mixed anhydride, or with a condensing agent. Examples include $CH_3$ COO—, $C_2$ $H_5$ COO—, tert-BuCOO—, $C_{15}$ $H_{31}$ COO—, PhCOO—, (m-NaOOCPh) COO—, NaOOC$CH_2$ $CH_2$ COO—, $CH_3$ CH($NH_2$)COO—, $CH_2$ N($CH_3$)$_2$ COO—, $CH_3$ $SO_3$—, $CH_3$ $CH_2$ $SO_3$—, $CF_3$ $SO_3$—, $CH_2$ $FSO_3$—, $CF_3$ $CH_2$ $SO_3$—, p-$CH_3$ O-PhSO$_3$ PhSO$_3$— and p-$CH_3$ PhSO$_3$.

The oligonucleotides of the present invention can be synthesized according to the usual methods with a compound of formula (I). For example, they can be easily synthesized by an automated nucleic acid synthesizer which is commercially available (e.g., the synthesizer by AppliedBiosystems, Dainippon Seiki or the like). A method for synthesizing is solid-phase synthesis using phosphoramidite, solid-phase synthesis using hydrogen phosphonate or the like. For example, it disclosed in Tetrahedron Letters 22, 1859-1862 (1981), WO2011/052436 or the like.

Bx in a nucleoside structure of formula (II) is preferably that its substituent is not protected with a protective group. Examples include the following groups.

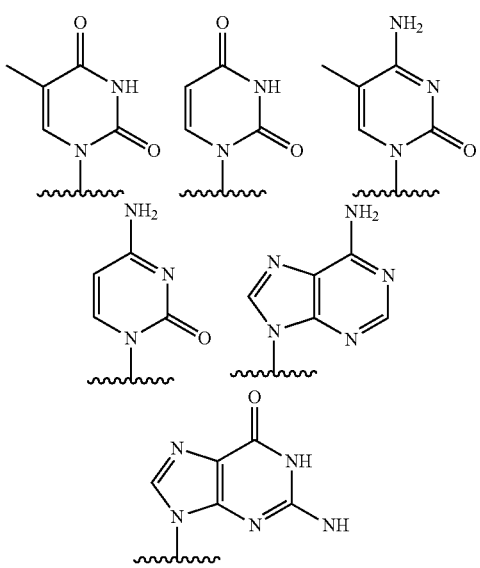

Therefore, when Bx in a compound of formula (I) has a substituent protected with a protective group, deprotection is carried out during the oligonucleotide synthesis.

The oligonucleotides of the present invention show the superior binding affinity to a single strand RNA and nuclease resistance. Therefore, the oligonucleotides are thought to have very good in vivo persistence. Then, compounds of formula (I) of the present invention are useful very much as materials for synthesizing nucleic acid pharmaceuticals (pharmaceutical compositions) such as antisense oligonucleotide and the like. The nucleic acid pharmaceuticals using the oligonucleotides of the present invention have the high affinity to the target molecule compared to unmodified nucleic acid pharmaceuticals, are difficult to degrade in vivo, and then show more stable effects.

A nucleic acid pharmaceutical using the oligonucleotides of the present invention may be administered in a number of ways depending upon whether local or systemic treatment is desired and upon the area to be treated. As an administration method, for example, it may be topical (including ophthalmic, intravaginal, intrarectal, intranasal and transdermal), oral or parenteral. Parenteral administration includes intravenous injection or drip infusion, subdermal, intraperitoneal or intramuscular injection, lung administration by aspiration or inhalation, intrathecal administration, intraventricular administration and the like.

When a nucleic acid pharmaceutical using the oligonucleotides of the present invention is topically administered, a formulation such as a transdermal patch, ointment, lotion, cream, gel, drop, suppository, spray, liquid, powder or the like can be used.

The composition for oral administration includes powder, granule, suspension or solution dissolved in water or non-aqueous vehicle, capsule, powder, tablet or the like.

The composition for parenteral, intrathecal or intraventricular administration includes sterile aqueous solutions which contain buffers, diluents and other suitable additives, or the like.

A nucleic acid pharmaceutical using oligonucleotides of the present invention may be manufactured by mixing an effective amount of a nucleic acid with various pharmaceutical additives suitable for the administration form, such as excipients, binders, moistening agents, disintegrants, lubricants, diluents and the like. When it is an injection, an active ingredient together with a suitable carrier can be sterilized to give a pharmaceutical composition.

Examples of the excipients include lactose, saccharose, glucose, starch, calcium carbonate, crystalline cellulose and the like. Examples of the binders include methylcellulose, carboxymethylcellulose, hydroxypropylcellulose, gelatin, polyvinylpyrrolidone and the like. Examples of the disintegrants include carboxymethylcellulose, sodium carboxymethylcellulose, starch, sodium alginate, powdered agar, sodium lauryl sulfate and the like. Examples of the lubricants include talc, magnesium stearate, macrogol and the like. Cacao oil, macrogol, methylcellulose or the like may be used as base materials of suppositories. When the composition is manufactured as solutions, emulsified injections or suspended injections, solubilizing agent, suspending agents, emulsifiers, stabilizers, preservatives, isotonic agents and the like which are usually used may be added. For oral administration, sweetening agents, flavors and the like which are usually used may be added.

Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in vivo. Persons of ordinary skill in the art can easily determine optimal dosages, dosing methodologies and repetition rates. Optimal dosages can be generally calculated based on IC50 or EC50 in vitro or in vivo animal experiments although they change according to relative efficacy of each nucleic acid pharmaceutical. Dosages shown as mg/kg are calculated according to the usual method when, for example, a molecular weight of a nucleic acid (derived from the nucleic acid sequence and chemical structure) and effective dosage such as IC50 (derived from experiments) are provided.

In this description, meaning of each abbreviation is as follows:
Ac: acetyl
Bn: benzyl
BOM: benzyloxymethyl
Bz: benzoyl
DMTr: dimethoxytrityl
i-Pr: isopropyl
Me: methyl
Ph: phenyl
Piv: pivaloyl
TBS: tert-butyldimethylsilyl
tBu: tert-butyl
Tf: trifluoromethanesulfonyl

EXAMPLES

The present invention is further explained by the following Examples, Reference Examples and Experiment Examples which are not intended to limit the scope of the present invention.

NMR analysis of compounds obtained in the examples was performed by 162 MHz, 300 MHz or 400 MHz using $CD_3OD$, $CDCl_3$ or DMSO-d6.

Example 1

Synthesis of a Nucleotide of the Present Invention (1-A) Synthesis of Compound I-1

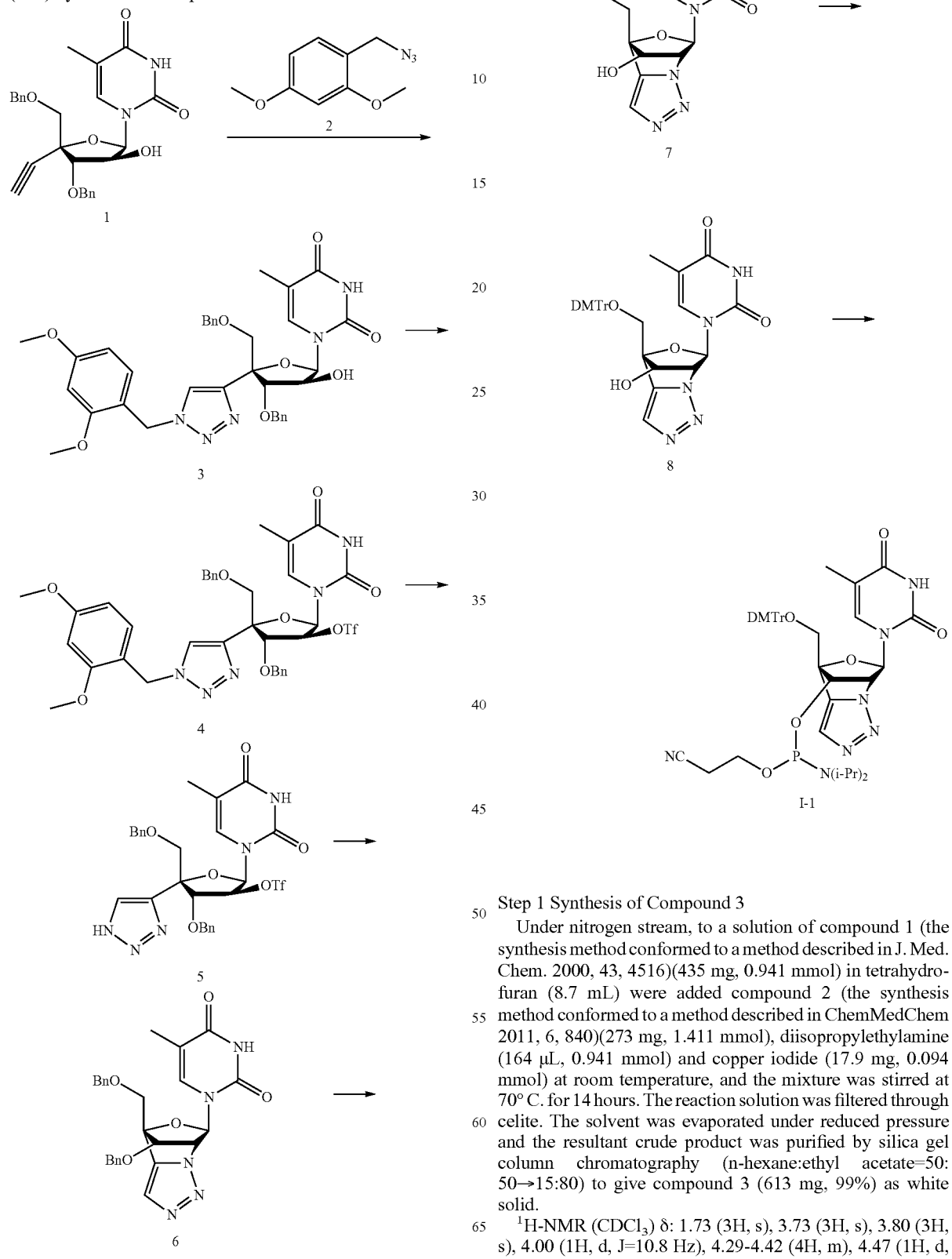

Step 1 Synthesis of Compound 3

Under nitrogen stream, to a solution of compound 1 (the synthesis method conformed to a method described in J. Med. Chem. 2000, 43, 4516)(435 mg, 0.941 mmol) in tetrahydrofuran (8.7 mL) were added compound 2 (the synthesis method conformed to a method described in ChemMedChem 2011, 6, 840)(273 mg, 1.411 mmol), diisopropylethylamine (164 μL, 0.941 mmol) and copper iodide (17.9 mg, 0.094 mmol) at room temperature, and the mixture was stirred at 70° C. for 14 hours. The reaction solution was filtered through celite. The solvent was evaporated under reduced pressure and the resultant crude product was purified by silica gel column chromatography (n-hexane:ethyl acetate=50:50→15:80) to give compound 3 (613 mg, 99%) as white solid.

$^1$H-NMR (CDCl$_3$) δ: 1.73 (3H, s), 3.73 (3H, s), 3.80 (3H, s), 4.00 (1H, d, J=10.8 Hz), 4.29-4.42 (4H, m), 4.47 (1H, d, J=11.6 Hz), 4.56 (1H, d, J=11.6 Hz), 4.63 (1H, d, J=11.2 Hz), 4.68 (1H, d, J=11.2 Hz), 5.40 (1H, d, J=14.4 Hz), 5.44 (1H, d, J=14.4 Hz), 6.25 (1H, d, J=3.9 Hz), 6.39-6.44 (2H, m), 7.03-7.09 (3H, m), 7.24-7.26 (3H, m), 7.30-7.39 (5H, m), 7.47 (1H, s), 7.57 (1H, s), 8.32 (1H, s).

Step 2 Synthesis of Compound 4

Under nitrogen stream, to a solution of compound 3 (589 mg, 0.899 mmol) in dichloromethane (5.9 mL) were added pyridine (239 μL, 2.97 mmol) and Trifluoromethanesulfonic anhydride (228 μL, 1.35 mmol) on ice-cooling, and the mixture was stirred for 40 minutes. To the reaction solution was added saturated sodium bicarbonate water, and the mixture was extracted with ethyl acetate. The organic layer was washed with water and brine, and then dried over sodium sulfate. The solvent was evaporated under reduced pressure to give the crude product of compound 4 (714 mg).

$^1$H-NMR (CDCl$_3$) δ: 1.68 (3H, s), 3.71 (3H, s), 3.81 (3H, s), 3.89 (1H, d, J=10.8 Hz), 3.97 (1H, d, J=10.8 Hz), 4.51-4.58 (3H, m), 4.66 (1H, d, J=11.6 Hz), 4.84 (1H, d, J=6.0 Hz), 5.40 (1H, d, J=14.8 Hz), 5.46 (1H, d, J=14.8 Hz), 5.58 (1H, t, J=6.0 Hz), 6.44-6.47 (2H, m), 6.57 (1H, d, J=6.0 Hz), 7.13-7.16 (3H, m), 7.26-7.36 (8H, m), 7.43 (1H, s), 7.46 (1H, s), 7.93 (1H, s).

Step 3 and Step 4 Synthesis of Compound 6

At room temperature, to a solution of the crude product of compound 4 (714 mg) in trifluoroacetic acid (10 mL) was added anisole (344 μL, 3.15 mmol), and the mixture was stirred at 50° C. for 2.5 hours. On ice-cooling, to the reaction solution was added methanol, and then the solvent was evaporated under reduced pressure. The resultant residue was coevaporated with methanol twice and toluene twice to give the crude product of compound 5 (983 mg).

At room temperature, to a solution of the crude product of compound 5 in acetonitrile (11 mL) was added potassium carbonate (311 mg, 2.25 mmol), and the mixture was stirred for 5 hours. To the reaction solution was added water, and the mixture was extracted with ethyl acetate. The organic layer was washed with water and brine, and then dried over anhydrous sodium sulfate. The solvent was evaporated and the resultant crude product was purified by silica gel column chromatography (n-hexane: ethyl acetate=70:30→25:75) to give compound 6 (339 mg, 77% (overall yield from Step 2 to Step 4)) as white solid.

$^1$H-NMR (CDCl$_3$) δ: 1.65 (3H, d, J=1.2 Hz), 4.14 (1H, d, J=11.2 Hz), 4.37 (1H, d, J=11.2 Hz), 4.54 (1H, d, J=11.6 Hz), 4.58 (1H, d, J=11.6 Hz), 4.65-4.68 (2H, m), 4.71 (1H, d, J=11.2 Hz), 5.27 (1H, s), 5.56 (1H, s), 7.10-7.12 (2H, m), 7.28-7.42 (8H, m), 7.56 (1H, d, J=1.2 Hz), 7.63 (1H, s), 8.44 (1H, s).

Step 5 Synthesis of Compound 7

To a solution of compound 6 (122 mg, 0.251 mmol) in ethanol (4.9 mL) were added ammonium formate (790 mg, 12.53 mmol) and 20% palladium hydroxide-carbon powder (60 mg), and the mixture was stirred at 85° C. for 5.5 hours. To the reaction solution were added ammonium formate (790 mg, 12.53 mmol) and 20% palladium hydroxide-carbon powder (60 mg), and the mixture was stirred at 85° C. for 1.5 hours. The reaction solution was filtered, and then the solvent was evaporated. The resultant crude product was purified by silica gel column chromatography (chloroform: methanol=100:0→85:15) to give compound 7 (18 mg, 24%) as white solid.

$^1$H-NMR (MeOD) δ: 1.93 (3H, s), 4.22 (1H, d, J=13.2 Hz), 4.41 (1H, d, J=13.2 Hz), 4.91 (1H, s), 5.22 (1H, s), 5.58 (1H, s), 7.75 (1H, s), 7.87 (1H, s).

Step 6 Synthesis of Compound 8

Under nitrogen stream, to a solution of compound 7 (17 mg, 0.055 mmol) in pyridine (0.5 mL) was added 4,4'-dimethoxytrityl chloride (28 mg, 0.083 mmol) at room temperature, and the mixture was stirred for 4 hours. At room temperature, 4,4'-dimethoxytrityl chloride (28 mg, 0.083 mmol) was added thereto, and the mixture was stirred for 3.5 hours. To the reaction solution was added saturated sodium bicarbonate water, and the mixture was extracted with ethyl acetate. The organic layer was washed with water and brine, and then dried over sodium sulfate. The solvent was evaporated under reduced pressure, and the resultant crude product was purified by silica gel column chromatography (chloroform:methanol=100:0→95:5) to give compound 8 (22 mg, 66%) as white solid.

$^1$H-NMR (CDCl$_3$) δ: 1.67 (3H, s), 3.78 (3H, s), 3.79 (3H, s), 3.89 (1H, d, J=11.6 Hz), 4.04 (1H, d, J=11.6 Hz), 4.09 (1H, br s), 5.12 (1H, s), 5.23 (1H, s), 5.87 (1H, s), 6.86 (4H, dd, J=8.8, 3.2 Hz), 7.32 (3H, t, J=7.5 Hz), 7.38 (4H, dd, J=8.8, 2.6 Hz), 7.49 (2H, d, J=7.5 Hz), 7.56 (1H, s), 7.74 (1H, s), 9.27 (1H, s).

Step 7 Synthesis of Compound I-1

Under nitrogen stream, to a solution of compound 8 (58 mg, 0.095 mmol) in anhydrous dichloromethane (0.9 mL) were added diisopropylethylamine (67 μL, 0.381 mmol) and 2-cyanoethyl-N,N-diisopropylchlorophosphoramidite (64 μL, 0.286 mmol), and the mixture was stirred for 4.5 hours. To the reaction solution was added saturated sodium bicarbonate water, and the mixture was extracted with ethyl acetate. The organic layer was washed with water and brine, and then dried over anhydrous sodium sulfate. The solvent was evaporated, and the resultant crude product was purified by silica gel column chromatography (n-hexane:ethyl acetate=66:34-25:75) to give compound I-1 (47 mg, 61%) as white solid.

$^{31}$P-NMR (CDCl$_3$) δ$_P$: 150.6, 150.7.

(1-B) Synthesis of Compound I-1

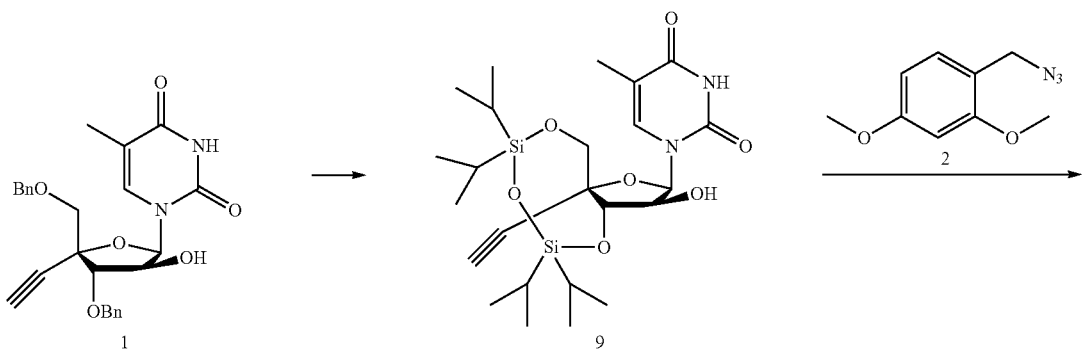

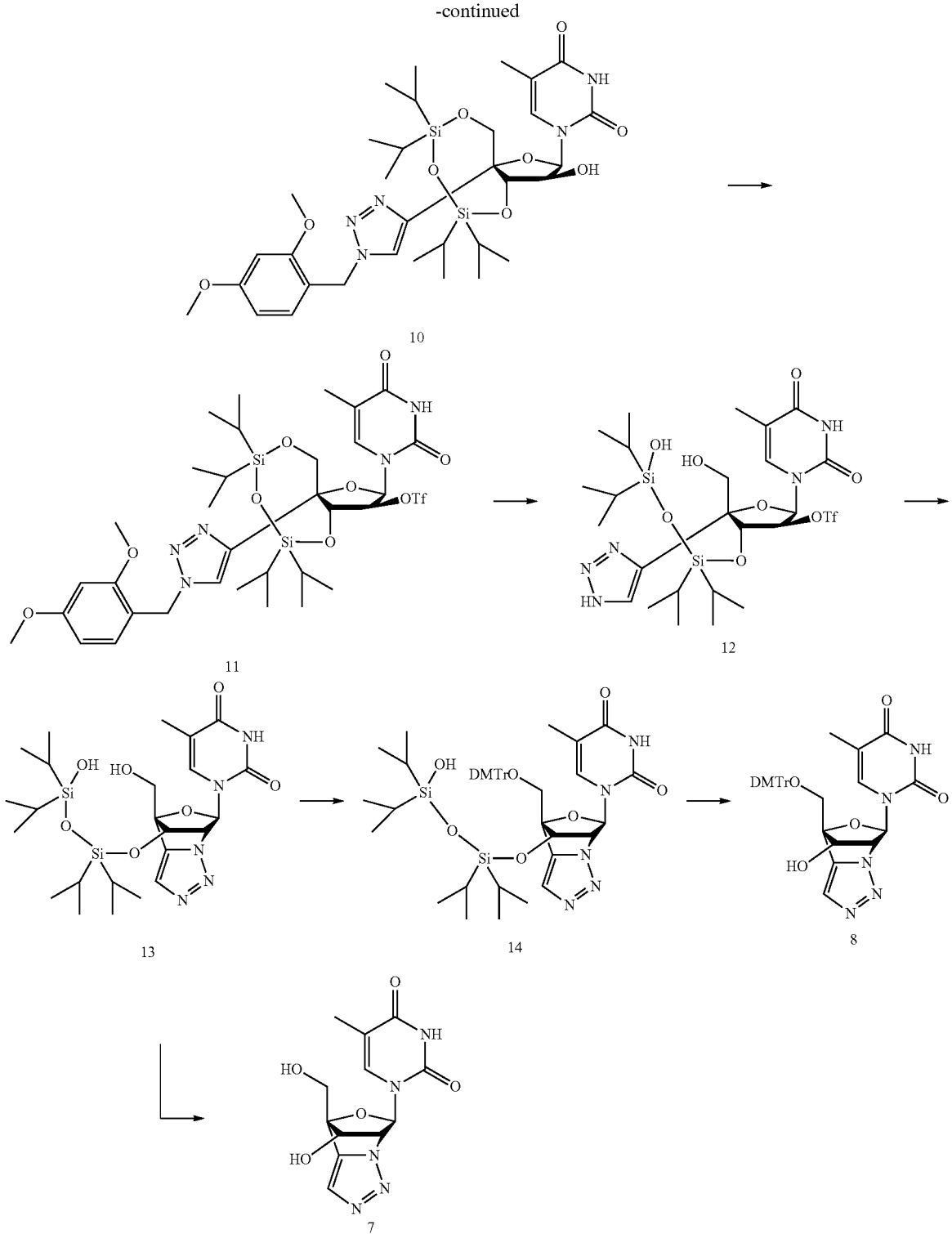

Step 1 Synthesis of Compound 9

Under nitrogen stream, to a solution of compound 1 (5.0 g, 9.92 mmol) in dichloromethane (25 mL) was added dropwise boron trichloride (1 mol/L dichloromethane solution, 49.6 mL, 49.6 mmol) at −78° C. The mixture was stirred for 30 minutes, and then stirred for 2 hours on ice-cooling. At −78° C., to the reaction solution were added dropwise methanol (50 mL) and pyridine (30 mL) The mixture was stirred for 10 minutes, and then heated to room temperature. The solvent was evaporated under reduced pressure, and to the resultant residue was added pyridine (20 mL). The deposited solids were removed by filtration. The filtrate was condensed and the resultant residue was dissolved in pyridine (25 mL). At room temperature, 1,3-dichloro-1,1,3,3-tetraisopropyldisiloxane (4.76 mL, 14.89 mmol) was added thereto, and the mixture was stirred overnight. To the reaction solution was added methanol (10 mL), and then the solvent was evaporated under reduced pressure. The resultant residue was dissolved in ethyl acetate, washed with 5% aqueous solution of citric acid and brine, and then dried over magnesium sulfate. The solvent was evaporated under reduced pressure, and the resultant crude product was purified by silica gel column chromatography (n-hexane: ethyl acetate=80:20→50:50) to give compound 9 (4.66 g, 90%) as white solid.

$^1$H-NMR (CDCl$_3$) δ: 1.07-1.13 (28H, m), 1.91 (3H, s), 2.63 (1H, s), 2.71 (1H, d, J=4.4 Hz), 3.96 (1H, d, J=13.2 Hz), 4.15 (1H, d, J=13.2 Hz), 4.23 (1H, d, J=8.8 Hz), 4.75-4.80 (1H, m), 6.16 (1H, d, J=6.4 Hz), 7.43 (1H, s), 8.30 (1H, s).

Step 2 Synthesis of Compound 10

Under nitrogen stream, to a solution of compound 9 (5.0 g, 9.53 mmol) in tetrahydrofuran (75 mL) were added compound 2 (2.40 g, 12.4 mmol), diisopropylethylamine (1.66 mL, 9.53 mmol) and copper iodide (181 mg, 0.953 mmol) at room temperature, and the mixture was stirred at 70° C. for 3 hours. The reaction solution was filtered through celite. The solvent was evaporated under reduced pressure, and the resultant crude product was purified by silica gel column chromatography (n-hexane:ethyl acetate=50:50→20:80) to give compound 10 (6.50 g, 95%) as white solid.

$^1$H-NMR (CDCl$_3$) δ: 0.85 (7H, s), 1.05-1.14 (21H, m), 1.92 (3H, s), 3.04 (1H, d, J=4.8 Hz), 3.82 (3H, s), 3.83 (3H, s), 3.98 (1H, d, J=12.8 Hz), 4.29 (1H, d, J=12.8 Hz), 4.47 (1H, d, J=8.8 Hz), 4.57-4.62 (1H, m), 5.44 (1H, d, J=14.4 Hz), 5.48 (1H, d, J=14.4 Hz), 6.08 (1H, d, J=6.4 Hz), 6.47-6.49 (2H, m), 7.20 (1H, d, J=8.8 Hz), 7.56 (1H, s), 7.61 (1H, s), 8.64 (1H, s).

Step 3, Step 4 and Step 5 Synthesis of Compound 13

Under nitrogen stream, to a solution of compound 10 (4.0 g, 5.59 mmol) in dichloromethane (40 mL) were added pyridine (1.98 mL, 24.57 mmol) and Trifluoromethanesulfonic anhydride (2.08 mL, 12.29 mmol) on ice-cooling, and the mixture was stirred for 5 hours. To the reaction solution was added 10% aqueous solution of citric acid (40 mL), and the mixture was extracted with ethyl acetate. The organic layer was washed with saturated sodium bicarbonate water, water and brine, and then dried over magnesium sulfate. The solvent was evaporated under reduced pressure to give the crude product of compound 11 (4.98 g).

At room temperature, to a solution of the crude product of compound 11 (4.98 g) in acetonitrile (90 mL) were added water (10 mL) and cerium (IV) ammonium nitrate (10.1 g, 18.45 mmol), the mixture was stirred for 7.5 hours. To the reaction solution were added saturated sodium bicarbonate water and ethyl acetate, and then the deposited solids were removed by filtration. The filtrate was extracted with ethyl acetate. The organic layer was washed with water and brine, and then dried over magnesium sulfate. The solvent was evaporated under reduced pressure to give the crude product of compound 12 (4.39 g).

At room temperature, to a solution of the crude product of compound 12 in acetonitrile (80 mL) was added potassium carbonate (1.93 g, 13.98 mmol), and the mixture was stirred at 50° C. for 7 hours. To the reaction solution was added water, and acetonitrile was evaporated under reduced pressure. The resultant residue was extracted with ethyl acetate. The organic layer was washed with water and brine, and then dried over magnesium sulfate. The solvent was evaporated, and the resultant crude product was purified by silica gel column chromatography (n-hexane:ethyl acetate=50:50→20:80) to give compound 13 (927 mg, 29% (overall yield from Step 3 to Step 5)) as white solid.

$^1$H-NMR (CDCl$_3$) δ: 0.84-1.02 (28H, m), 1.93 (3H, s), 4.24-4.27 (3H, m), 4.48 (1H, d, J=12.0 Hz), 5.20 (1H, s), 5.28 (1H, s), 5.68 (1H, s), 7.63 (1H, s), 7.77 (1H, s), 9.19 (1H, br s).

Step 6 Synthesis of Compound 7

To a solution of compound 13 (202 mg, 0.355 mmol) in tetrahydrofuran (2.0 mL) was added a solution of 1 mmol/L tetra-n-butyl ammonium fluoride in tetrahydrofuran (426 μL, 0.426 mmol) at room temperature, and the mixture was stirred for 30 minutes. The solvent was evaporated, and then the resultant crude product was purified by silica gel column chromatography (ethyl acetate: methanol=100:0→85:15) to give compound 7 (101 mg, 92%) as white solid.

Step 7 and step 8 Synthesis of Compound 8

Under nitrogen stream, to a solution of compound 13 (589 mg, 1.036 mmol) in pyridine (10 mL) was added 4,4'-dimethoxytrityl chloride (702 mg, 2.073 mmol) at room temperature, and the mixture was stirred for 45 hours. After the solvent was evaporated under reduced pressure, to the residue was added saturated sodium bicarbonate water, and the mixture was extracted with ethyl acetate. The organic layer was washed with water and brine, and then dried over sodium sulfate. The solvent was evaporated under reduced pressure to give the crude product of compound 14 (1.37 g).

At room temperature, to a solution of the crude product of compound 14 (1.37 g) in tetrahydrofuran (14 mL) were added triethylamine (431 μL, 3.11 mmol) and triethylamine trihydrofluoride (1.01 mL, 6.22 mmol), and the mixture was stirred for 30 minutes. To the reaction solution was added saturated sodium bicarbonate water, and the mixture was extracted with ethyl acetate. The organic layer was washed with water and brine, and then dried over sodium sulfate. The solvent was evaporated, and the resultant crude product was purified by silica gel column chromatography (chloroform: methanol=100:0→94:6) to give compound 8 (626 mg, 99%) as white solid.

Synthesis of Compound I-1

From compound 7 obtained in Step 6, compound I-1 was given through Step 6 and Step 7 of (1-A).

From compound 8 obtained in Step 8, compound I-1 was given through Step 7 of (1-A).

(2) Synthesis of Compound I-2

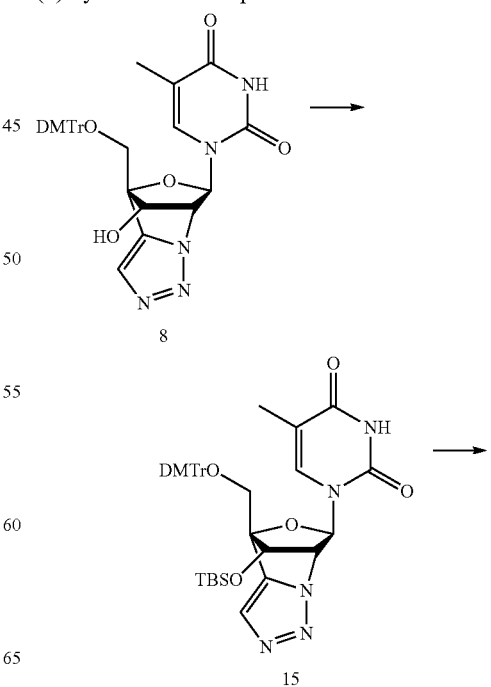

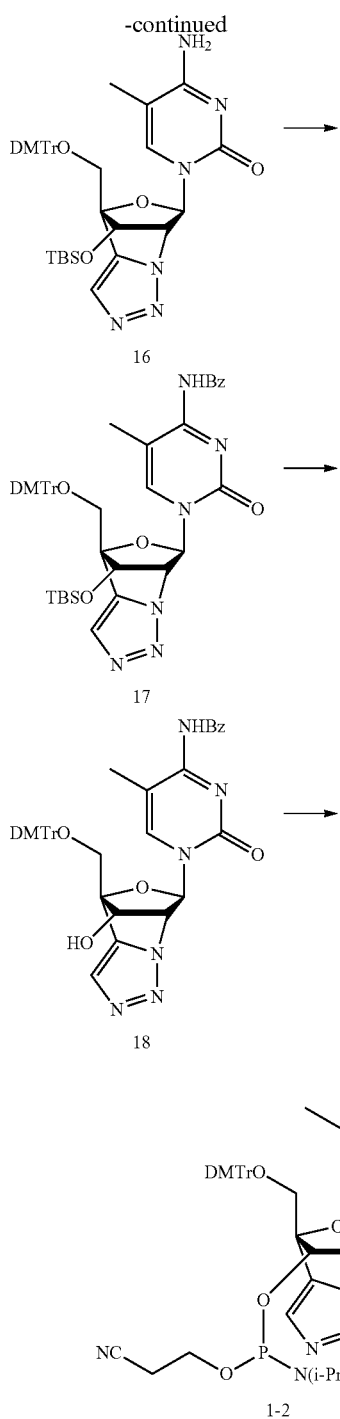

Step 1 Synthesis of Compound 15

Under nitrogen stream, to a solution of compound 8 obtained in Step 6 of (1-A) or Step 8 of (1-B) (70 mg, 0.115 mmol) in N,N-dimethylformamide (0.49 mL) were added imidazole (47 mg, 0.689 mmol) and t-butyldimethylchlorosilane (69 mg, 0.459 mmol) at room temperature, and the mixture was stirred for 5 days. To the reaction solution was added water, and the mixture was extracted with ethyl acetate. The organic layer was washed with water and brine, and then dried over sodium sulfate. The solvent was evaporated under reduced pressure, and the resultant crude product was purified by silica gel column chromatography (n-hexane:ethyl acetate=75:25→445:55) to give compound 15 (76 mg, 91%) as white solid.

$^1$H-NMR (CDCl$_3$) δ: −0.03 (3H, s), 0.02 (3H, s), 0.61 (9H, s), 1.68 (3H, s), 3.65 (1H, d, J=11.2 Hz), 3.80 (6H, s), 4.05 (1H, d, J=11.2 Hz), 5.06 (1H, s), 5.29 (1H, s), 5.57 (1H, s), 6.86 (4H, dd, J=8.8, 4.4 Hz), 7.27-7.37 (7H, m), 7.46 (2H, d, J=7.6 Hz), 7.55 (1H, s), 7.84 (1H, s), 8.25 (1H, s).

Step 2 and Step 3 Synthesis of Compound 17

Under nitrogen stream, to a solution of compound 15 (75 mg, 0.103 mmol) in acetonitrile (0.75 mL) were added triethylamine (57 μL, 0.414 mmol), N,N-dimethylaminopyridine (2.5 mg, 0.021 mmol) and 2,4,6-triisopropylbenzenesulfonyl chloride (47 mg, 0.155 mmol) at room temperature, and the mixture was stirred for 16 hours. At room temperature, to the reaction solution was added 28% ammonia water (0.75 mL), and the mixture was stirred for 2 hours. The solvent was evaporated under reduced pressure. To the resultant residue was added water, and the mixture was extracted with ethyl acetate. The organic layer was washed with water and brine, and then dried over sodium sulfate. The solvent was evaporated under reduced pressure to give the crude product of compound 16 (113 mg).

Under nitrogen stream, to a solution of the crude product of compound 16 in N,N-dimethylformamide (0.52 mL) was added anhydrous benzoic acid (30 mg, 0.134 mmol) at room temperature, and the mixture was stirred for 18 hours. To the reaction solution was added saturated sodium bicarbonate water, and the mixture was extracted with ethyl acetate. The organic layer was washed with water and brine, and then dried over anhydrous sodium sulfate. The solvent was evaporated, and the resultant crude product was purified by silica gel column chromatography (n-hexane: ethyl acetate=80: 20→60:40) to give compound 17 (59 mg, 69%) as white solid.

$^1$H-NMR (CDCl$_3$) δ: −0.04 (3H, s), 0.02 (3H, s), 0.60 (9H, s), 1.87 (3H, s), 3.66 (1H, d, J=11.2 Hz), 3.81 (6H, s), 4.08 (1H, d, J=11.2 Hz), 5.08 (1H, s), 5.35 (1H, s), 5.63 (1H, s), 6.88 (4H, dd, J=8.8, 5.6 Hz), 7.29-7.40 (7H, m), 7.44-7.57 (6H, m), 8.00 (1H, s), 8.33 (2H, d, J=7.6 Hz), 13.44 (1H, s).

Step 4 Synthesis of Compound 18

At room temperature, to a solution of compound 17 (58 mg, 0.070 mmol) in tetrahydrofuran (0.9 mL) were added triethylamine (29 μL, 0.211 mmol) and triethylamine trihydrofluoride (69 μL, 0.422 mmol), and the mixture was stirred for 2 hours. To the reaction solution was added saturated sodium bicarbonate water, and the mixture was extracted with ethyl acetate. The organic layer was washed with water and brine, and then dried over anhydrous sodium sulfate. The solvent was evaporated, and the resultant crude product was purified by silica gel column chromatography (chloroform: methanol=100:0→495:5) to give compound 18 (47 mg, 93%) as white solid.

$^1$H-NMR (CDCl$_3$) δ: 1.90 (3H, s), 3.35 (1H, br s), 3.81 (3H, s), 3.81 (3H, s), 3.90 (1H, d, J=11.6 Hz), 4.10 (1H, d, J=11.6 Hz), 5.08 (1H, s), 5.25 (1H, s), 5.71 (1H, s), 6.89 (4H, dd, J=8.8, 4.8 Hz), 7.28-7.55 (12H, m), 7.59 (1H, s), 7.89 (1H, s), 8.32 (2H, d, J=5.2 Hz), 13.30 (1H, s).

Step 5 Synthesis of Compound I-2

Under nitrogen stream, to a solution of compound 18 (45 mg, 0.063 mmol) in anhydrous acetonitrile-tetrahydrofuran (0.9 mL, 1:1) were added 2-cyanoethyl-N,N,N',N'-tetraisopropyl phosphordiamidite (40 μL, 0.127 mmol) and 5-ethylthio-1H-tetrazole (12 mg, 0.095 mmol), and the mixture was stirred for 4.5 hours. To the reaction solution was added saturated sodium bicarbonate water, and the mixture was extracted with ethyl acetate. The organic layer was washed with water and brine, and then dried over anhydrous sodium sulfate. The solvent was evaporated, and the resultant crude product was purified by silica gel column chromatography (n-hexane:ethyl acetate=65:35→45:55) to give compound I-2 (56 mg, 97%) as white solid.

$^{31}$P-NMR (CDCl$_3$) δ$_P$: 150.8.

(3) Synthesis of Compound VII-1

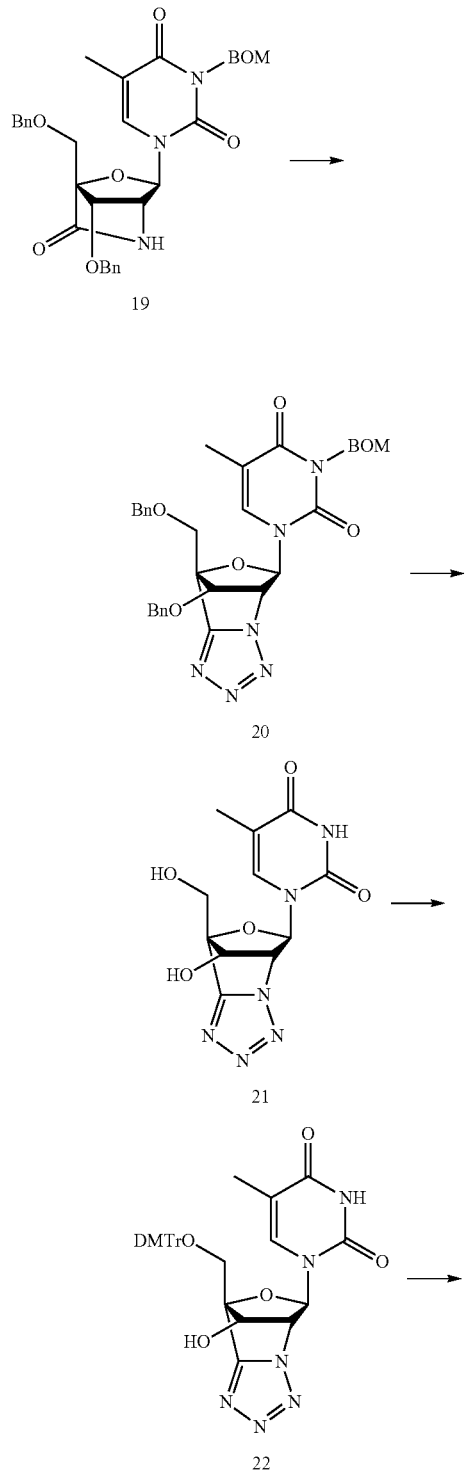

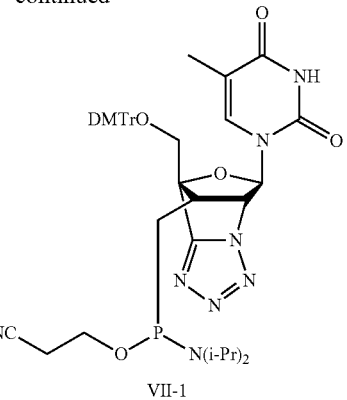

VII-1

Step 1 Synthesis of Compound 20

Under nitrogen stream, to a solution of compound 19 (the synthesis method conformed to a method described in WO2011/052436)(276 mg, 0.472 mmol) in acetonitrile (2.7 mL) were added 2,4,6-trimethylpyridine (187 μL, 1.416 mmol) and Trifluoromethanesulfonic anhydride (159 μL, 0.944 mmol) on ice-cooling, and mixture was stirred for 1.5 hours. On ice-cooling, to the reaction solution was added sodium azide (123 mg, 1.888 mmol), and the mixture was stirred at room temperature for 1.5 hours. To the reaction solution was added water, and the mixture was extracted with ethyl acetate. The organic layer was washed with 2 mol/L aqueous hydrochloric acid, water and brine, and then dried over sodium sulfate. The solvent was evaporated under reduced pressure, and the resultant crude product was purified by silica gel column chromatography (n-hexane: ethyl acetate=90:10→60:40) to give compound 20 (182 mg, 63%) as white solid.

$^1$H-NMR (CDCl$_3$) δ: 1.65 (3H, s), 4.26 (1H, d, J=11.6 Hz), 4.55-4.57 (3H, m), 4.67 (1H, d, J=11.2 Hz), 4.72-4.74 (4H, m), 5.24 (1H, s), 5.45 (1H, d, J=9.6 Hz), 5.48 (1H, d, J=9.6 Hz), 5.52 (1H, s), 7.06-7.08 (2H, m), 7.26-7.39 (13H, m), 7.52 (1H, s).

Step 2 Synthesis of Compound 21

To a suspension of compound 20 (180 mg, 0.296 mmol) in methanol (7.5 mL) was added 20% palladium hydroxide-carbon powder (90 mg), and the mixture was stirred under hydrogen stream at room temperature for 18 hours. To the reaction solution was added pyridine, and the mixture was filtered. The solvent was evaporated and the resultant residue was dissolved in methanol\|pyridine (1/1, 5.0 mL). To the solution was added 28% ammonia water (2.0 mL) at room temperature, and the mixture was stirred for 30 minutes. The solvent was evaporated to give compound 21 (98 mg) as white solid. $^1$H-NMR (DMSO-d$_6$) δ: 1.86 (3H, d, J=1.2 Hz), 4.17 (1H, dd, J=13.2, 6.0 Hz), 4.42 (1H, dd, J=13.2, 6.0 Hz), 4.96 (1H, d, J=4.0 Hz), 5.34 (1H, s), 5.82 (1H, s), 5.91 (1H, t, J=6.0 Hz), 6.75 (1H, d, J=4.0 Hz), 7.80 (1H, d, J=1.2 Hz), 11.58 (1H, s).

Step 3 Synthesis of Compound 22

Under nitrogen stream, to a solution of compound 21 (72 mg, 0.232 mmol) in pyridine (1.0 mL) were added 4,4'-dimethoxytrityl chloride (134 mg, 0.395 mmol) at room temperature, and the mixture was stirred for 20 hours. After the solvent was evaporated under reduced pressure, to the residue was added saturated sodium bicarbonate water, and the mixture was extracted with ethyl acetate. The organic layer was washed with water and brine, and then dried over sodium sulfate. The solvent was evaporated under reduced pressure, and the resultant crude product was purified by silica gel column chromatography (n-hexane: ethyl acetate=55:45→30:70) to give compound 22 (96 mg, 68%) as white solid.

$^1$H-NMR (CDCl$_3$) δ: 1.58 (3H, s), 3.75 (3H, s), 3.76 (3H, s), 4.02 (1H, d, J=12.0 Hz), 4.12 (1H, br s), 4.31 (1H, d, J=12.0 Hz), 5.26 (1H, s), 5.31 (1H, s), 5.85 (1H, s), 6.84 (4H, dd, J=8.4, 3.6 Hz), 7.20-7.31 (3H, m), 7.36 (4H, dd, J=8.4, 4.8 Hz), 7.46 (2H, d, J=7.6 Hz), 7.79 (1H, s), 9.48 (1H, br s).

Step 4 Synthesis of Compound VII-1

Under nitrogen stream, to a solution of compound 22 (179 mg, 0.293 mmol) in acetonitrile (2.7 mL) were added 2-cyanoethyl-N,N,N',N'-tetraisopropyl phosphordiamidite (149 μL, 0.496 mmol) and 5-ethylthio-1H-tetrazole (50 mg, 0.381 mmol) at room temperature, and the mixture was stirred for 15 hours. To the reaction solution was added saturated sodium bicarbonate water, and the mixture was extracted with ethyl acetate. The organic layer was washed with water and brine, and then dried over anhydrous sodium sulfate. The solvent was evaporated, and the resultant crude product was purified by silica gel column chromatography (n-hexane:ethyl acetate=50:50→25:75) to give compound VII-1 (211 mg, 89%) as white solid.

$^{31}$P-NMR (CDCl$_3$) δ$_P$: 150.9, 151.5.

(4) Synthesis of Compound IV-1

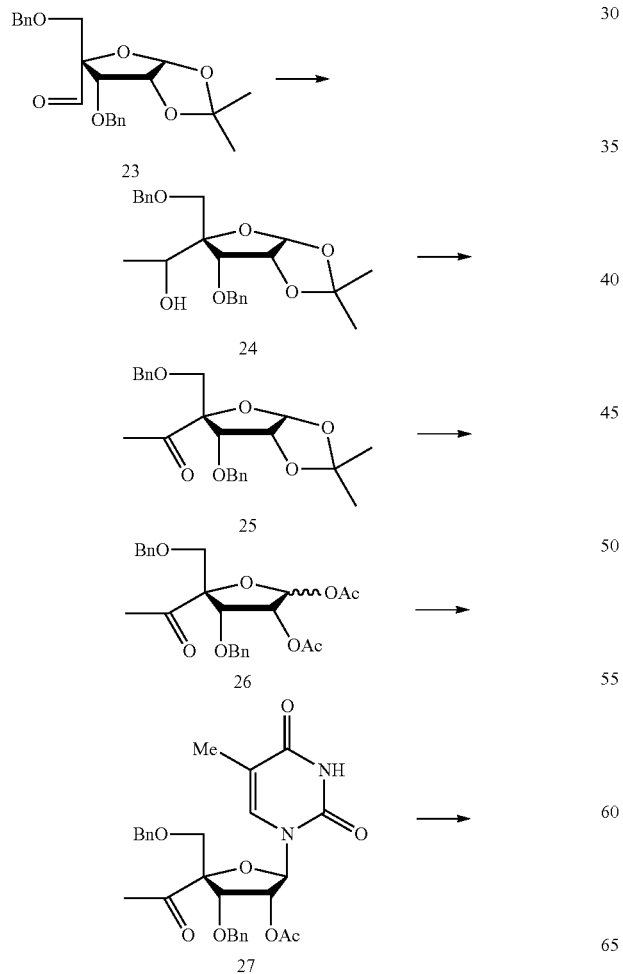
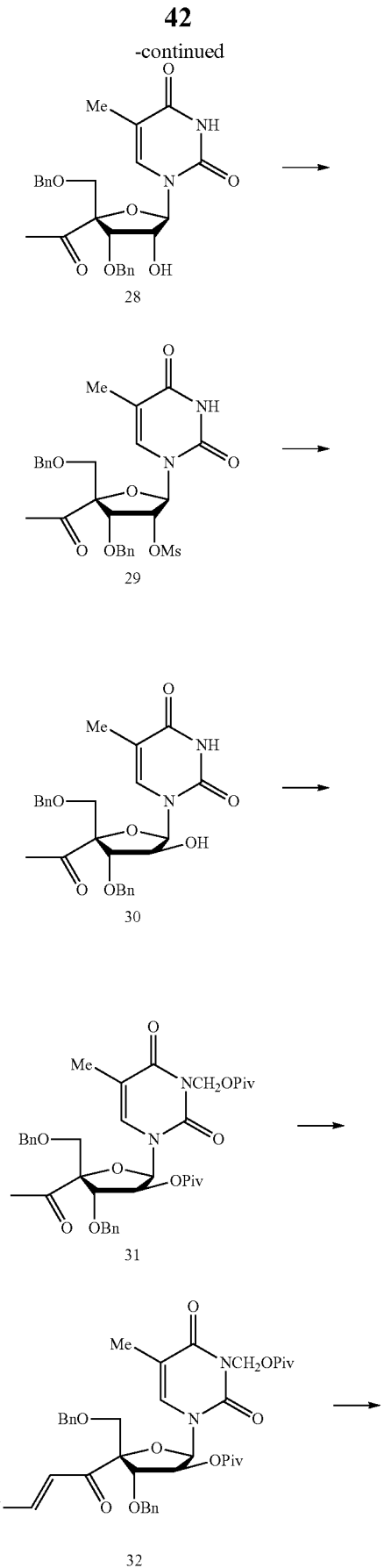

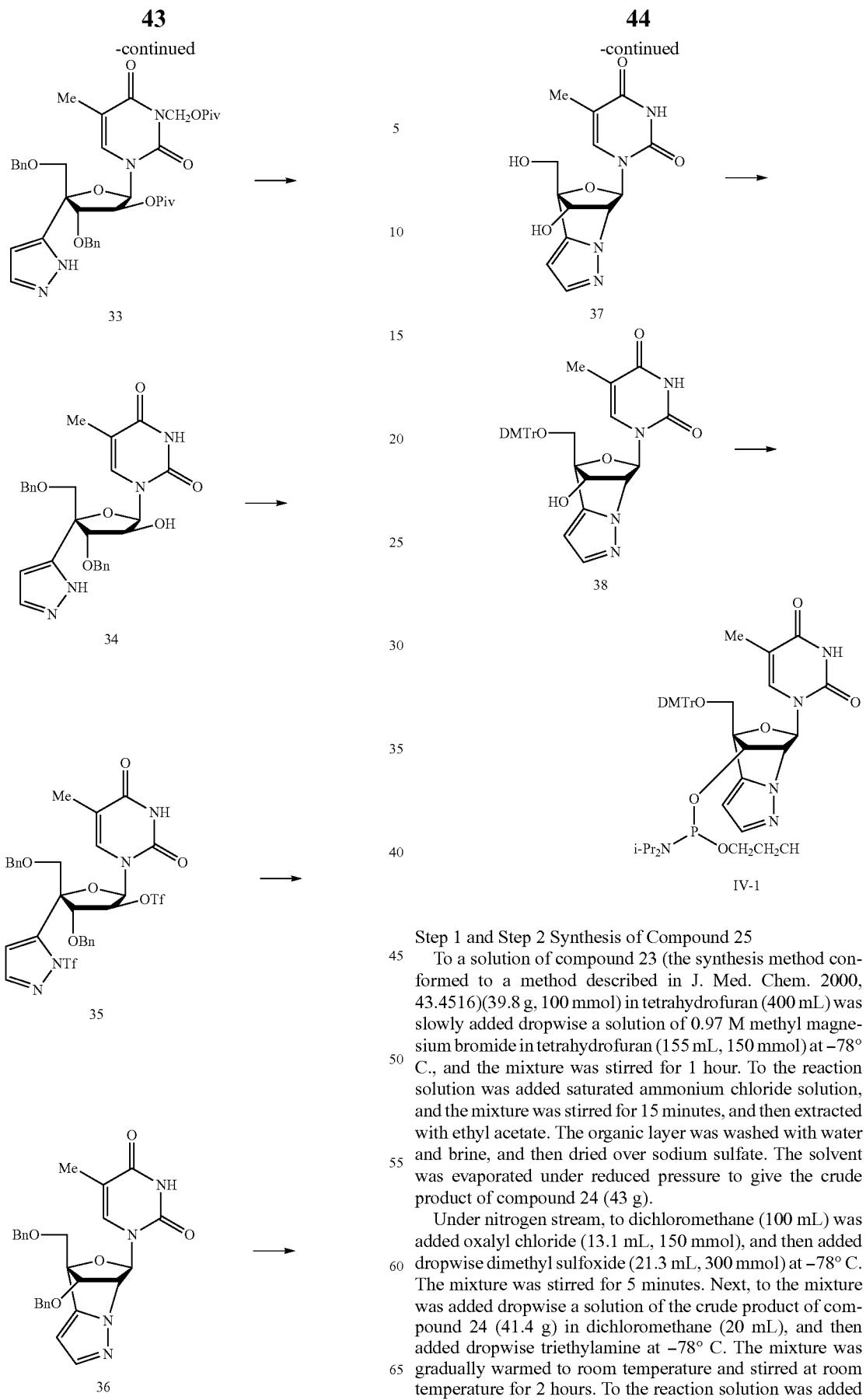

Step 1 and Step 2 Synthesis of Compound 25

To a solution of compound 23 (the synthesis method conformed to a method described in J. Med. Chem. 2000, 43.4516)(39.8 g, 100 mmol) in tetrahydrofuran (400 mL) was slowly added dropwise a solution of 0.97 M methyl magnesium bromide in tetrahydrofuran (155 mL, 150 mmol) at −78° C., and the mixture was stirred for 1 hour. To the reaction solution was added saturated ammonium chloride solution, and the mixture was stirred for 15 minutes, and then extracted with ethyl acetate. The organic layer was washed with water and brine, and then dried over sodium sulfate. The solvent was evaporated under reduced pressure to give the crude product of compound 24 (43 g).

Under nitrogen stream, to dichloromethane (100 mL) was added oxalyl chloride (13.1 mL, 150 mmol), and then added dropwise dimethyl sulfoxide (21.3 mL, 300 mmol) at −78° C. The mixture was stirred for 5 minutes. Next, to the mixture was added dropwise a solution of the crude product of compound 24 (41.4 g) in dichloromethane (20 mL), and then added dropwise triethylamine at −78° C. The mixture was gradually warmed to room temperature and stirred at room temperature for 2 hours. To the reaction solution was added water to quench, and extracted with dichloromethane. The organic layer was washed with water and brine, and then dried over sodium sulfate. The resultant crude product was purified by silica gel column chromatography (n-hexane:ethyl acetate=95:5→65:35) to give compound 25 (28.5 g, 69.1% (overall yield from Step 1 to Step 2)) as light yellow foam.

$^1$H-NMR (CDCl$_3$) δ: 1.39 (3H, s), 1.58 (3H, s), 2.39 (3H, s), 3.50 (1H, d, J=10.1 Hz), 3.78 (1H, d, J=10.1 Hz), 4.12 (1.0H, d, J=5.3 Hz), 4.42-4.50 (3H, m), 4.72-4.75 (2H, m), 5.97 (1H, d, J=4.0 Hz), 7.22-7.33 (10H, m).

Step 3 and Step 4 Synthesis of Compound 27

To a solution of compound 25 (28.5 g, 69.1 mmol) in acetic acid (138 mL) were added concentrated sulfuric acid (74 μL, 1.382 mmol) and anhydrous acetic acid (52.8 mL, 559 mmol) at room temperature, and the mixture was stirred for 4 hours. The reaction solution was poured into saturated sodium bicarbonate water, and then the mixture was extracted with ethyl acetate. The organic layer was washed with water and brine, and then dried over sodium sulfate. The solvent was evaporated under reduced pressure to give the crude product of compound 26 (29.1 g).

Under nitrogen stream, to a solution of the crude product of compound 26 (29.1 g) in acetonitrile (146 mL) were added thymine (10.5 g, 83 mmol) and N,O-bis(trimethylsilyl)acetamide (55.2 mL, 223 mmol) at room temperature, and the mixture was stirred at 50° C. for 5 minutes. At room temperature, trimethylsilyl trifluoromethanesulfonate (11.54 mL, 63.7 mmol) was added thereto, and the mixture was heated to reflux for 1.5 hours. To the reaction solution was added saturated sodium bicarbonate water, and the mixture was extracted with ethyl acetate. The organic layer was washed with water and brine, and then dried over sodium sulfate. The solvent was evaporated under reduced pressure to give the crude product of compound 27 (33 g) as white solid.

$^1$H-NMR (CDCl$_3$) δ: 1.55 (3H, s), 2.04 (3H, s), 2.30 (3H, s), 3.66 (1H, d, J=10.4 Hz), 4.03 (1H, d, J=10.4 Hz), 4.42 (1H, d, J=10.9 Hz), 4.52 (1H, d, J=10.9 Hz), 4.53 (1H, d, J=5.3 Hz), 4.57 (1.2H, d, J=11.4 Hz), 4.68 (1H, d, J=11.4 Hz), 5.32 (1H, dd, J=8.1, 5.3 Hz), 6.57 (1H, d, J=8.1 Hz), 7.22-7.38 (10H, m), 7.52 (1H, s) 8.01 (1H, s).

Step 5 Synthesis of Compound 28

To a solution of the crude product of compound 27 (33 g) in tetrahydrofuran (330 mL) was added 40% aqueous solution of methylamine (27 mL), and the mixture was stirred on ice-cooling for 1.5 hours. After tetrahydrofuran was evaporated under reduced pressure, to the residue was added water, and the mixture was extracted with ethyl acetate. The organic layer was washed with water and brine, and then dried over sodium sulfate. The solvent was evaporated under reduced pressure, and the resultant crude product was purified by silica gel column chromatography (n-hexane:ethyl acetate=80:20→50:50) to give compound 28 (14.1 g, 47% (overall yield from Step 3 to Step 5)) as white solid.

$^1$H-NMR (CDCl$_3$) δ: 1.55 (3H, s), 2.29 (3H, s), 3.63 (1H, d, J=10.4 Hz), 4.01 (1H, d, J=10.4 Hz), 4.24 (1H, d, J=4.8 Hz), 4.40 (1H, brs), 4.54 (1H, d, J=11.4 Hz), 4.59 (1H, d, J=11.4 Hz), 4.62 (1H, d, J=11.4 Hz), 4.67 (1H, d, J=11.4 Hz), 6.35 (1H, d, J=7.8 Hz) 7.26-7.38 (10H, m), 7.49 (1H, s), 9.81 (1H, brs).

Step 6 Synthesis of Compound 29

Under nitrogen stream, to a solution of compound 28 (14 g) in dichloromethane (70 mL) were added triethylamine (10.1 mL, 72.8 mmol) and methanesulfonyl chloride (2.72 mL, 35.0 mmol) at room temperature, and the mixture was stirred for 45 minutes. After the solvent was evaporated under reduced pressure, to the residue was added water, and the mixture was extracted with ethyl acetate. The organic layer was washed with water and brine, and then dried over sodium sulfate. The solvent was evaporated under reduced pressure to give the crude product of compound 29 (16.3 g).

$^1$H-NMR (CDCl$_3$) δ: 1.56 (3H, s), 2.29 (3H, s), 2.98 (3H, s), 3.66 (1H, d, J=10.4 Hz), 4.01 (1H, d, J=10.4 Hz), 4.44 (1H, d, J=5.0 Hz), 4.57 (2H, d, J=11.2 Hz), 4.68 (1H, d, J=11.2), 4.69 (1H, d, J=11.2), 5.39 (1H, dd, J=7.8, 5.0 Hz), 6.55 (1H, d, J=7.8 Hz), 7.26-7.40 (10H, m), 7.49 (1H, s), 8.08 (1H, brs).

Step 7 Synthesis of Compound 30

To a solution of the crude product of compound 29 (16.3 g) in tetrahydrofuran (81 mL) was added 1 mol/L aqueous solution of sodium hydroxide (81 mL), and the mixture was stirred at room temperature for 2 hours. N,N-dimethylformamide (35 mL) was added thereto, and then the mixture was stirred at 70° C. for 18 hours. The mixture was quenched with saturated ammonium chloride solution, and tetrahydrofuran was evaporated under reduced pressure. Then, to the residue was added water, and the mixture was extracted with ethyl acetate. The organic layer was washed with water and brine, and then dried over sodium sulfate. The solvent was evaporated under reduced pressure, and the resultant crude product was purified by silica gel column chromatography (n-hexane:ethyl acetate=60:40→10:90) to give compound 30 (14.1 g) as white solid.

$^1$H-NMR (CDCl$_3$) δ: 1.69 (3H, s), 2.25 (3H, s), 3.87 (1H, d, J=10.1 Hz), 4.05 (1H, d, J=10.1 Hz), 4.06 (1H, s), 4.43 (1H, d, J=11.6 Hz), 4.55-4.58 (4H, m), 6.41 (1H, s), 7.17-7.35 (10H, m), 7.46 (1H, s).

Step 8 Synthesis of Compound 31

Under nitrogen stream, to a solution of compound 30 (2.68 g, 5.58 mmol) in N,N-dimethylformamide (25 mL) were added sodium carbonate (3.08 g, 22.3 mmol) and chloromethyl pivalate (1.83 mL, 12.3 mmol) on ice-cooling, and the mixture was stirred at 50° C. for 10 hours. Saturated ammonium chloride solution was added thereto, and the mixture was stirred. The mixture was extracted with ethyl acetate. The organic layer was washed with water and brine, and then dried over sodium sulfate. To a solution of the resultant crude product in N,N-dimethylformamide (20 mL) were added sodium carbonate (1.86 g, 13.5 mmol) and chloromethyl pivalate (1.11 mL, 7.41 mmol), and the mixture was stirred at 50° C. for 16 hours. To the reaction solution was added saturated ammonium chloride solution, and the mixture was stirred. The mixture was extracted with ethyl acetate, and the organic layer was washed with water and brine. After drying over sodium sulfate, the solvent was evaporated under reduced pressure, and the resultant crude product was purified by silica gel column chromatography (n-hexane:ethyl acetate=65:35→50:50) to give compound 31 (2.8 g, 73%) as white solid.

$^1$H-NMR (CDCl$_3$) δ: 0.97 (9H, s), 1.18 (9H, s), 1.88 (3H, s), 2.30 (3H, s), 3.63 (1H, d, J=9.6 Hz), 3.92 (1H, d, J=9.6 Hz), 3.97 (1H, m), 4.45 (1H, d, J=12.1 Hz), 4.54 (1H, d, J=11.6 Hz), 4.62 (1H, d, J=12.1 Hz), 4.73 (1H, d, J=11.6 Hz), 5.43 (1H, d, J=4.3 Hz), 5.94 (1H, t, J=9.9 Hz), 6.59 (1H, d, J=3.5 Hz), 7.23-7.37 (10H, m), 7.48 (1H, s).

Step 9 and Step 10 Synthesis of Compound 33

Under nitrogen stream, compound 31 (800 mg, 1.18 mmol) was dissolved in N,N-dimethylformamide dimethyl acetal (313 μL, 2.36 mmol), and the mixture was stirred at 110° C. for 1 hour. To the reaction solution was added water, and the mixture was extracted with ethyl acetate. The organic layer was washed with water and brine, and then dried over sodium sulfate. The solvent was evaporated under reduced pressure to give the crude product of compound 32 (865 mg).

Under nitrogen stream, to a solution of the crude product of compound 32 (865 mg) in ethanol (8 mL) was added hydrazine monohydrate (68.8 μL, 1.42 mmol) at room temperature, and the mixture was stirred at 80° C. for 1 hour. To the reaction solution was added saturated ammonium chloride solution, and the mixture was stirred. The mixture was extracted with ethyl acetate, and the organic layer was washed with water and brine. After drying over sodium sulfate, the solvent was evaporated under reduced pressure, and the resultant crude product was purified by silica gel column chromatography (n-hexane: ethyl acetate=90:10→65:35) to give compound 33 (815 mg, 98% (overall yield from Step 9 to Step 10)) as white solid.

$^1$H-NMR (CDCl$_3$) δ: 1.06 (9H, s). 1.17 (9H, s), 1.67 (3H, s), 3.86 (1H, d, J=10.7 Hz), 3.91 (1H, d, 10.7 Hz), 4.52 (1H, d, J=13.1 Hz), 4.58 (1H, d, J=13.1 Hz), 4.59 (1H, d, J=13, 1 Hz), 4.70 (1H, d, J=13.1 Hz), 4.76 (1H, d, J=6.6 Hz), 5.56 (1H, t, J=6.6 Hz), 5.89 (1H, d, J=9.3 Hz), 5.92 (1H, d, J=9.3 Hz), 6.37 (1H, d, J=1.8 Hz), 6.62 (1H, d, J=6.6 Hz), 7.24-7.36 (10H, m), 7.51 (1H, s), 7.55 (1.1H, d, J=1.8 Hz).

Step 11 Synthesis of Compound 34

To a solution of compound 33 (4.1 g, 5.83 mmol) in ethanol (41 mL) was added 2 mol/L aqueous solution of sodium hydroxide (10 mL, 20 mmol) at room temperature, and the mixture was stirred at 50° C. for 1 hour. On ice-cooling, to the reaction solution was added saturated ammonium chloride solution, and the mixture was stirred for 10 minutes. The mixture was extracted with ethyl acetate. The organic layer was washed with water and brine, and then dried over sodium sulfate. The solvent was evaporated under reduced pressure, and the resultant crude product was purified by silica gel column chromatography (n-hexane:ethyl acetate=60:40→415:85) to give compound 34 (1.9 g, 65%) as white solid.

$^1$H-NMR (CDCl$_3$) δ: 1.55 (3H, s), 3.84 (1H, d, J=10.6 Hz), 3.95 (1H, d, J=10.6 Hz), 4.49 (1H, s), 4.53 (1H, d, J=12.0 Hz), 4.56 (1H, d, J=12.0 Hz), 4.64 (1H, d, J=12.0 Hz), 4.78 (1H, d, J=12.0 Hz), 6.26 (1H, s), 6.37 (1H, d, J=3.5 Hz), 7.22-7.35 (11H, m), 7.48 (1H, s), 7.71 (1H, s).

Step 12 and Step 13 Synthesis of Compound 36

Under nitrogen stream, to a solution of compound 34 (1.0 g, 1.98 mmol) in dichloromethane (10 mL) were added pyridine (0.8 mL, 9.91 mmol) and trifluoromethanesulfonic anhydride (0.737 mL, 4.36 mmol) on ice-cooling, and the mixture was stirred for 1 hour. To the reaction solution was added water, and the mixture was extracted with ethyl acetate. The organic layer was washed with water and brine, and then dried over sodium sulfate. The solvent was evaporated under reduced pressure to give the crude product of compound 35 (1.4 g).

Under nitrogen stream, to a solution of the crude product of compound 35 (1.4 g) in acetonitrile (14 mL), was added 1 mol/L aqueous solution of sodium hydroxide (7.0 ml, 7.0 mmol) at room temperature, and the mixture was stirred for 2 hours. To the reaction solution was added saturated ammonium chloride solution, and the mixture was stirred. Acetonitrile was evaporated under reduced pressure. The residue was extracted with ethyl acetate, and the organic layer was washed with water and brine. After drying over sodium sulfate, the solvent was evaporated under reduced pressure, and the resultant crude product was purified by silica gel column chromatography (n-hexane: ethyl acetate=65:35-40:60) to give compound 36 (403 mg, 42% (overall yield from Step 12 to Step 13)) as white solid.

$^1$H-NMR (CDCl$_3$) δ: 1.63 (3H, s) 4.17 (1H, d, J=11.4 Hz), 4.35 (1H, d, J=11.4 Hz), 4.53 (1H, s), 4.54 (1H, d, J=12.8 Hz), 4.60 (1H, d, J=12.8), 4.67 (1H, d, J=11.4 Hz), 4.70 (1H, d, J=11.4 Hz), 5.13 (1.H, s), 5.20 (1H, s), 6.21 (1H, s), 7.15-7.40 (11H, m), 7.55 (1H, s), 7.57 (1H, s), 8.08 (1H, brs).

Step 14 Synthesis of Compound 37

To a solution of compound 36 (445 mg, 0.914 mmol) in tetrahydrofuran (5 mL), was added 20% palladium hydroxide-carbon powder (250 mg) at room temperature, and the mixture was stirred under hydrogen stream for 3 hours. After filtration through celite, it washed with warm methanol. The solvent was evaporated under reduced pressure to give the crude product of compound 37 (291 mg).

$^1$H-NMR (MeOD) δ: 1.92 (3H, s), 4.21 (1H, d, J=13.0 Hz), 4.39 (1H, d, J=13.0 Hz), 4.78 (1H, s), 5.01 (1H, s), 5.15 (1H, s), 6.33 (1H, s), 7.54 (1H, s), 7.89 (1H, s).

Step 15 Synthesis of Compound 38

Under nitrogen stream, to a solution of the crude product of compound 37 (291 mg) in pyridine (3.0 mL) was added 4,4'-dimethoxytrityl chloride (465 mg, 1.37 mmol) at room temperature, and the mixture was stirred for 2 hours. To the reaction solution was added saturated sodium bicarbonate water, and the mixture was extracted with ethyl acetate. The organic layer was washed with water and brine, and then dried over sodium sulfate. The solvent was evaporated under reduced pressure, and the resultant crude product was purified by silica gel column chromatography (n-hexane: ethyl acetate=60:40→35:65) to give compound 38 (242 mg, 44% (overall yield from Step 14 to Step 15)) as white solid.

$^1$H-NMR (CDCl$_3$) δ: 1.67 (3H, s), 3.79 (6H, s), 3.83 (1H, d, J=8.6 Hz), 4.02 (1H, d, J=8.6 Hz), 4.96 (1H, s), 5.08 (1H, s), 5.34 (1H, s), 6.17 (1H, s), 7.50-6.75 (15H, m), 7.77 (1H, s), 8.68 (1H, brs).

Step 16 Synthesis of compound IV-1

Under nitrogen stream, to a solution of compound 38 (230 mg, 0.378 mmol) in dichloromethane (2.8 mL) were added diisopropylethylamine (198 μL, 1.13 mmol) and 2-cyanoethyl-N,N,-diisopropylchlorophosphoramidite (101 μL, 0.45 mmol) at room temperature, and the mixture was stirred for 1 hour. To the reaction solution was saturated sodium bicarbonate water, and the mixture was extracted with ethyl acetate. The organic layer was washed with water and brine, and then dried over anhydrous sodium sulfate. The solvent was evaporated, and the resultant crude product was purified by silica gel column chromatography (n-hexane:ethyl acetate=50:50→25:75) to give compound IV-1 (214 mg, 71%) as white solid.

$^{31}$P-NMR (CDCl$_3$) δ: 149.6, 150.3.

Similarly, the following nucleotides can be synthesized.

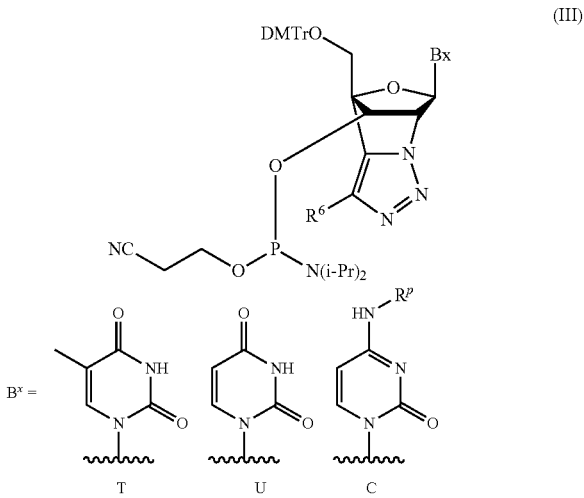

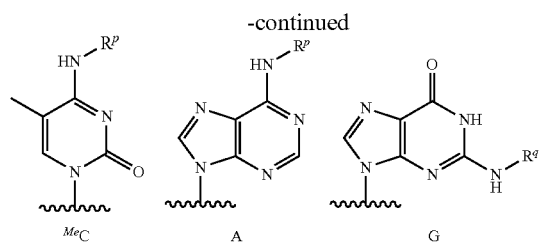

wherein $R^p$ is acetyl, benzoyl or phenoxyacetyl, and $R^q$ is isobutyryl, acetyl, benzoyl or phenoxyacetyl.

TABLE 1

| Compound | Bx | $R^6$ |
|---|---|---|
| III-1 | $^{Me}C$ | H |
| III-2 | A | H |
| III-3 | G | H |
| III-4 | T | Me |
| III-5 | $^{Me}C$ | Me |
| III-6 | A | Me |
| III-7 | G | Me |
| III-8 | T | OMe |
| III-9 | $^{Me}C$ | OMe |
| III-10 | A | OMe |
| III-11 | G | OMe |
| III-12 | T | C(=O)NHMe |
| III-13 | $^{Me}C$ | C(=O)NHMe |
| III-14 | A | C(=O)NHMe |
| III-15 | G | C(=O)NHMe |
| III-16 | T | NHC(=O)Me |
| III-17 | $^{Me}C$ | NHC(=O)Me |
| III-18 | A | NHC(=O)Me |
| III-19 | G | NHC(=O)Me |

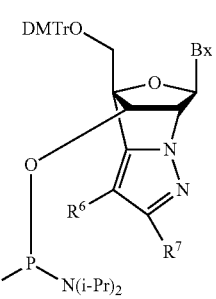
(IV)

TABLE 2

| Compound | Bx | $R^6$ | $R^7$ |
|---|---|---|---|
| IV-1 | T | H | H |
| IV-2 | $^{Me}C$ | H | H |
| IV-3 | A | H | H |
| IV-4 | G | H | H |
| IV-5 | T | H | Me |
| IV-6 | $^{Me}C$ | H | Me |
| IV-7 | A | H | Me |
| IV-8 | G | H | Me |
| IV-9 | T | Me | H |
| IV-10 | $^{Me}C$ | Me | H |
| IV-11 | A | Me | H |
| IV-12 | G | Me | H |
| IV-13 | T | Me | Me |
| IV-14 | $^{Me}C$ | Me | Me |
| IV-15 | A | Me | Me |
| IV-16 | G | Me | Me |

TABLE 2-continued

| Compound | Bx | $R^6$ | $R^7$ |
|---|---|---|---|
| IV-17 | T | H | OMe |
| IV-18 | $^{Me}C$ | H | OMe |
| IV-19 | A | H | OMe |
| IV-20 | G | H | OMe |
| IV-21 | T | H | C(=O)NHMe |
| IV-22 | $^{Me}C$ | H | C(=O)NHMe |
| IV-23 | A | H | C(=O)NHMe |
| IV-24 | G | H | C(=O)NHMe |
| IV-25 | T | H | NHC(=O)Me |
| IV-26 | $^{Me}C$ | H | NHC(=O)Me |
| IV-27 | A | H | NHC(=O)Me |
| IV-28 | G | H | NHC(=O)Me |

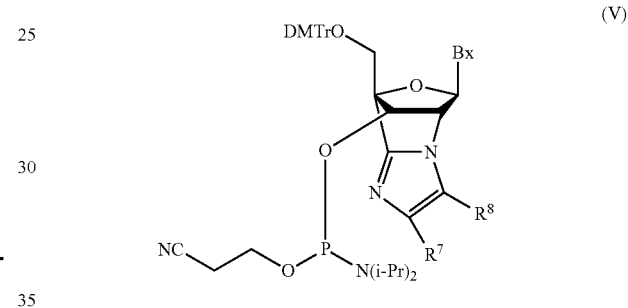
(V)

TABLE 3

| Compound | Bx | $R^7$ | $R^8$ |
|---|---|---|---|
| V-1 | T | H | H |
| V-2 | $^{Me}C$ | H | H |
| V-3 | A | H | H |
| V-4 | G | H | H |
| V-5 | T | H | Me |
| V-6 | $^{Me}C$ | H | Me |
| V-7 | A | H | Me |
| V-8 | G | H | Me |
| V-9 | T | Me | H |
| V-10 | $^{Me}C$ | Me | H |
| V-11 | A | Me | H |
| V-12 | G | Me | H |
| V-13 | T | Me | Me |
| V-14 | $^{Me}C$ | Me | Me |
| V-15 | A | Me | Me |
| V-16 | G | Me | Me |
| V-17 | T | OMe | H |
| V-18 | $^{Me}C$ | OMe | H |
| V-19 | A | OMe | H |
| V-20 | G | OMe | H |
| V-21 | T | C(=O)NHMe | H |
| V-22 | $^{Me}C$ | C(=O)NHMe | H |
| V-23 | A | C(=O)NHMe | H |
| V-24 | G | C(=O)NHMe | H |
| V-25 | T | NHC(=O)Me | H |
| V-26 | $^{Me}C$ | NHC(=O)Me | H |
| V-27 | A | NHC(=O)Me | H |
| V-28 | G | NHC(=O)Me | H |

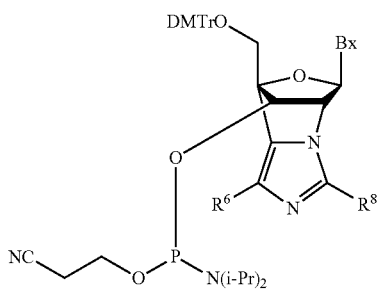

(VI)

TABLE 4

| Compound | Bx | R⁶ | R⁸ |
| --- | --- | --- | --- |
| VI-1 | T | H | H |
| VI-2 | $^{Me}$C | H | H |
| VI-3 | A | H | H |
| VI-4 | G | H | H |
| VI-5 | T | H | Me |
| VI-6 | $^{Me}$C | H | Me |
| VI-7 | A | H | Me |
| VI-8 | G | H | Me |
| VI-9 | T | Me | H |
| VI-10 | $^{Me}$C | Me | H |
| VI-11 | A | Me | H |
| VI-12 | G | Me | H |
| VI-13 | T | Me | Me |
| VI-14 | $^{Me}$C | Me | Me |
| VI-15 | A | Me | Me |
| VI-16 | G | Me | Me |
| VI-17 | T | OMe | H |
| VI-18 | $^{Me}$C | OMe | H |
| VI-19 | A | OMe | H |
| VI-20 | G | OMe | H |
| VI-21 | T | C(=O)NHMe | H |
| VI-22 | $^{Me}$C | C(=O)NHMe | H |
| VI-23 | A | C(=O)NHMe | H |
| VI-24 | G | C(=O)NHMe | H |
| VI-25 | T | NHC(=O)Me | H |
| VI-26 | $^{Me}$C | NHC(=O)Me | H |
| VI-27 | A | NHC(=O)Me | H |
| VI-28 | G | NHC(=O)Me | H |

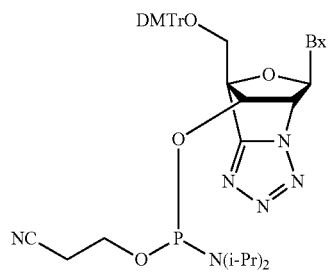

(VII)

TABLE 5

| Compound | Bx₁ |
| --- | --- |
| VII-2 | $^{Me}$C |
| VII-3 | A |
| VII-4 | G |

Example 2

Synthesis of the Oligonucleotides of the Present Invention (1) The Oligonucleotides Having a Nucleoside Structure(s) of Compound I-1

The oligonucleotides (1) to (5) (Table 6) prepared with compound I-1 obtained in (1-A) or (1-B) of Example 1 were synthesized by nS-8 (GeneDesign, Inc.) on the 0.2 µmol scale. Compound I-1 (an amidite unit) was dissolved in acetonitrile to use. In Table 6, a nucleoside structure of compound I-1 (the following formula II-1) is indicated by X. Duration of the coupling reaction between an amidite unit (compound I-1) and a hydroxyl group at 5'-terminus was extended from 32 seconds (standard condition) to 16 minutes. The oligonucleotide with the 5'-terminus protected with a DMTr group supported on a solid phase was treated with 28% ammonia water: 40% methylamine aqueous solution (1:1) at room temperature for oligonucleotide (1) to (4) and with 28% ammonia water at 55° C. for oligonucleotide (5), and then the solvent was evaporated. The resultant crude product was partially purified by Sep-Pak C18 Plus Short Cartridge (Waters), and then purified by reversed-phase HPLC (Gilson PLC2020, using WatersXBridge™ Shield RP18 Column 5.0 µm (10 mm×50 mm) and YMC Hydrosphere C18 Column 5.0 µm (10 mm×150 mm) as a preparative column).

The purities of the synthesized oligonucleotides were determined using reversed-phase HPLC, using WatersXBridge™ C18 Column 5.0 µm (4.6 mm×50 mm) (condition: gradient 5→8% (v/v) acetonitrile in 0.1 M triethyl ammonium acetate buffer (pH 7.0), 1 mL/min for 30 minutes) and YMC Hydrosphere C18 Column 5.0 µm (4.6 mm×100 mm)) (condition: gradient % (v/v) acetonitrile in 0.01 M triethyl ammonium acetate buffer (pH 7.0), 1 mL/min for 30 minutes and gradient 7.5→11.5% (v/v) acetonitrile, 1 mL/min for 30 minutes). The molecular weights were determined by ESI-TOF-MASS. The results are shown in Table 6.

TABLE 6

| Oligonucleotide | ESI-TOF-MASS Calculated ([M − H]⁻) | Found ([M − H]⁻) |
| --- | --- | --- |
| 5'-d(GCG TTX TTT GCT)-3' (1) | 3695.61 | 3695.62 |
| 5'-d(GCG TTX TXT GCT)-3' (2) | 3760.61 | 3760.63 |
| 5'-d(GCG XTX TXT GCT)-3' (3) | 3825.61 | 3825.75 |
| 5'-d(GCG TTX XXT GCT)-3' (4) | 3825.61 | 3825.73 |
| 5'-d(TTT TTT TTT X)-3' (5) | 3042.50 | 3042.58 |

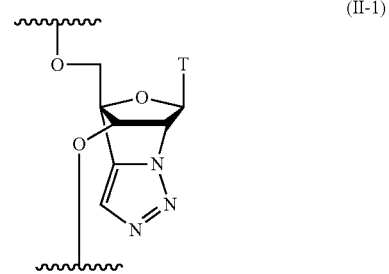

(II-1)

(2) The Oligonucleotides Having a Nucleoside Structure(s) of Compound IV-1

The oligonucleotides (8) to (12) was synthesized with compound IV-1 obtained in (4) of Example 1 by a method similar to (1). The molecular weights determined by ESI-TOF-MASS were shown in Table 7. In Table 7, a nucleoside structure of compound IV-1 (the following formula II-2) is indicated by Xp.

TABLE 7

| Oligonucleotide | ESI-TOF-MASS | |
|---|---|---|
| | Calculated ([M − H]⁻) | Found ([M − H]⁻) |
| 5'-d(GCG TTXp TTT GCT)-3' (8) | 3694.62 | 3694.69 |
| 5'-d(GCG TTXp TXpT GCT)-3' (9) | 3758.62 | 3758.71 |
| 5'-d(GCG XpTXp TXpT GCT)-3' (10) | 3822.63 | 3822.71 |
| 5'-d(GCG TTXp XpXpT GCT)-3' (11) | 3822.63 | 3822.70 |
| 5'-d (TTT TTT TTT Xp)-3' (12) | 3041.50 | 3041.59 |

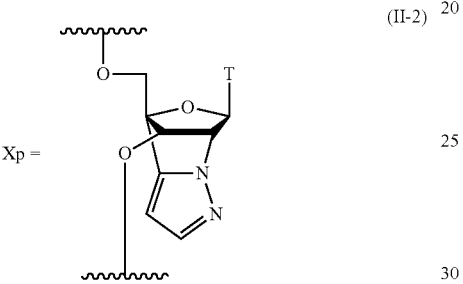

(II-2)

(3) The Oligonucleotides Having a Nucleoside Structure(s) of Compound VII-1

The oligonucleotides (13) to (17) was synthesized with compound VII-1 obtained in (3) of Example 1 by a method similar to (1). The molecular weights determined by ESI-TOF-MASS were shown in Table 8. In Table 8, a nucleoside structure of compound VII-1 (the following formula II-3) is indicated by Xq.

TABLE 8

| Oligonucleotide | ESI-TOF-MASS | |
|---|---|---|
| | Calculated ([M − H]⁻) | Found ([M − H]⁻) |
| 5'-d(GCG TTXq TTT GCT)-3' (13) | 3696.61 | 3696.69 |
| 5'-d(GCG TTXq TXqT GCT)-3' (14) | 3762.60 | 3762.68 |
| 5'-d(GCG XqTXq TXqT GCT)-3' (15) | 3828.60 | 3828.68 |
| 5'-d(GCG TTXq XqXqT GCT)-3' (16) | 3828.60 | 3828.68 |
| 5'-d(TTT TTT TTT Xq)-3' (17) | 3043.49 | 3043.57 |

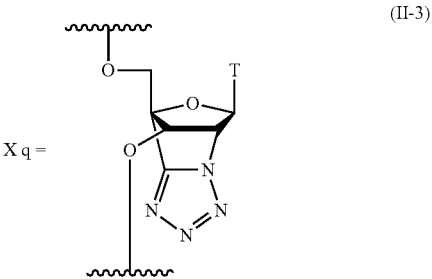

(II-3)

Reference Example 1

Synthesis of an Amide-Bridged Oligonucleotide

By reference to WO2011/052436, an amide-bridged amidite was synthesized. The amide-bridged oligonucleotide (6) was synthesized by a similar method to a method for the oligonucleotide (1) of Example 2 (1). The molecular weights were determined by MALDI-TOF-MASS. The results are shown in Table 9.

TABLE 9

| Oligonucleotide | MALDI-TOF-MASS | |
|---|---|---|
| | Calculated (M + H⁺) | Found (M + H⁺) |
| 5'-d(GCG TTV TTT GCT)-3' (6) | 3739.49 | 3739.04 |
| 5'-d(GCG TTW TTT GCT)-3' (7) | 3844.61 | 3845.25 |

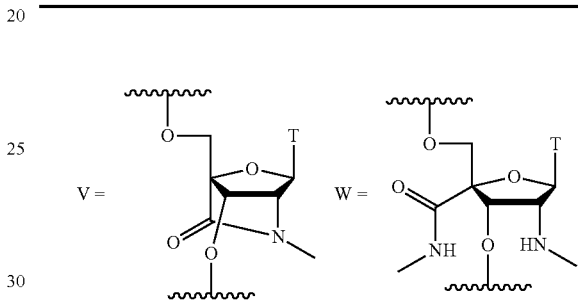

As a result of synthesis of the oligonucleotide (6), ring-opening (the oligonucleotide (7)) was confirmed in about 12% of the bridge parts. On the other hand, as a result of synthesis of the oligonucleotides (1) to (5), (8) to (12) in Example 2 (heterocyclyl bridge), ring-opening was not confirmed at all. Therefore, using the nucleotide (amidite) of the present invention, oligonucleotide(s) can be synthesized stably without by-products by general methods for synthesizing. So, the nucleotides of the present invention are thought to be useful as materials for synthesizing nucleic acid pharmaceuticals.

Example 3

Determination of the Melting Temperature (Tm) of the Oligonucleotides of the Present Invention (1) The Oligonucleotides Having a Nucleoside Structure(s) of Compound I-1

After the oligonucleotides (1) to (4) (antisense strands), which were the oligonucleotides synthesized in Example 2(1), and the sense strand (3'-CGC AAA AAA CGA-5') were subjected to an annealing treatment, their Tm values were measured to determine the hybridization ability of the oligonucleotides (1) to (4). The nucleotide (0), which nucleoside moieties of the oligonucleotide are unmodified, is used as a control.

The sample solution (150 μM) containing 100 mM NaCl, 10 mM sodium phosphate buffer (pH 7.2), 4.0 μM oligonucleotide (antisense strand) and 4.0 μM sense strand was heated in heating blocks (95° C.) for 5 minutes, and then cooled to room temperature over 12 hours. Nitrogen stream was passed through the cell chamber of the spectrophotometer (SHIMADZU UV-1800) to prevent dew condensation, and the sample solution was gradually cooled to 5° C. and kept at 5°

C. for 15 minutes before starting the measurements. The temperature was raised to 90° C. at the rate of 0.5° C./min while ultraviolet absorption spectra were measured at 260 nm at intervals of 0.5° C. Lidded cells were used to prevent concentration change due to rising temperature. The results are shown in Table 10.

TABLE 10

| Antisense strand | Sense strand | |
|---|---|---|
| | RNA complementary strand $T_m$ ($\Delta T_m$/mod.) (° C.) | DNA complementary strand $T_m$ ($\Delta T_m$/mod.) (° C.) |
| 5'-d(GCG TTT TTT GCT)-3' (0) | 49.3 | 53.1 |
| 5'-d(GCG TTX TTT GCT)-3' (1) | 52.1 (2.8) | 52.4 (−0.7) |
| 5'-d(GCG TTX TXT GCT)-3' (2) | 55.6 (3.2) | 51.1 (−1.0) |
| 5'-d(GCG XTX TXT GCT)-3' (3) | 60.1 (3.6) | 50.4 (−0.9) |
| 5'-d(GCG TTX XXT GCT)-3' (4) | 56.6 (2.4) | 48.3 (−1.6) |

(2) The Oligonucleotides Having a Nucleoside Structure(s) of Compound IV-1

After the oligonucleotides (8) to (11), which were the oligonucleotides synthesized in Example 2(2), and sense strand (3'-CGC AAA AAA CGA-5') were subjected to an annealing treatment, their Tm values were measured. The method for determining the Tm values was a method similar to (1). The results are shown in Table 11.

TABLE 11

| Antisense strand | Sense strand | |
|---|---|---|
| | RNA complementary strand $T_m$ ($\Delta T_m$/mod.) (° C.) | DNA complementary strand $T_m$ ($\Delta T_m$/mod.) (° C.) |
| 5'-d(GCG TTT TTT GCT)-3' (0) | 49.3 | 53.1 |
| 5'-d(GCG TTXp TTT GCT)-3' (8) | 52.2 (2.9) | 52.0 (−1.1) |
| 5'-d(GCG TTXp TXpT GCT)-3' (9) | 55.6 (3.1) | 50.2 (−1.4) |
| 5'-d(GCG XpTXp TXpT GCT)-3' (10) | 60.9 (3.9) | 49.2 (−1.3) |
| 5'-d(GCG TTXp XpXpT GCT)-3' (11) | 57.5 (2.7) | 48.0 (−1.7) |

(3) The Oligonucleotides Having a Nucleoside Structure(s) of Compound VII-1

After mixing the oligonucleotides (13) to (16), which were the oligonucleotides synthesized in Example 2(3), and sense strand (3'-CGC AAA AAA CGA-5'), their Tm values were measured. The method for determining the Tm values was a method similar to (1). The results are shown in Table 12.

TABLE 12

| Antisense strand | Sense strand | |
|---|---|---|
| | RNA complementary strand $T_m$ ($\Delta T_m$/mod.) (° C.) | DNA complementary strand $T_m$ ($\Delta T_m$/mod.) (° C.) |
| 5'-d(GCG TTT TTT GCT)-3' (0) | 49.7 | 54.0 |
| 5'-d(GCG TTX TTT GCT)-3' (13) | 52.3 (2.6) | 52.4 (−1.6) |
| 5'-d(GCG TTX TXT GCT)-3' (14) | 54.3 (2.3) | 50.3 (−1.9) |
| 5'-d(GCG XTX TXT GCT)-3' (15) | 58.1 (2.8) | 48.7 (−1.8) |
| 5'-d(GCG TTX XXT GCT)-3' (16) | 53.2 (1.2) | 45.5 (−2.8) |

As shown in Tables 10 to 12, the Tm values of the oligonucleotides of the present invention hybridized to the RNA complementary strand are higher than that of the natural oligonucleotide hybridized to the RNA complementary strand. On the other hand, the Tm values of the oligonucleotides of the present invention hybridized to the DNA complementary strand are lower than that of the natural oligonucleotide hybridized to the DNA complementary strand. In addition, the higher the rate of the nucleoside structure (II-1 to II-3) of the present invention comprised in the oligonucleotide, the higher the Tm value it has. Therefore, oligonucleotides prepared with a nucleotide(s) of the present invention have high affinities to single-stranded RNA, and they are easy to act on mRNA. Furthermore, they have low affinities to single-stranded DNA, and therefore, their effects on DNA replication are little and concern of the toxicity is low. Thus, the oligonucleotides of the invention are useful as materials for synthesizing nucleic acid pharmaceuticals.

Example 4

Assessment of Nuclease Resistance of the Oligonucleotides of the Present Invention The oligonucleotide (5) (Triazole BNA), the oligonucleotide (12) (Pyrazole BNA) and the oligonucleotide (17) (Tetrazole BNA) synthesized in Example 2 were subjected to a test for determining the resistance to an exonuclease, which degrades an oligonucleotide from the 3' terminus. The nucleotide (nature) wherein the X part of the oligonucleotide (5) was unmodified, and the nucleotide (LNA) wherein the X part of the oligonucleotide (5) was the following 2',4'-BNA/LNA were used as a control.

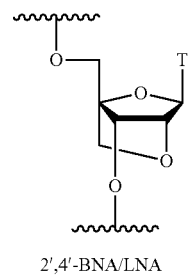

2',4'-BNA/LNA

A buffer solution containing 750 pmol of the oligonucleotide (80 μL) was kept at 37° C. for 5 minutes, and then mixed with a buffer solution (20 μL) containing 0.2 μg phosphodiesterase I (Worthington Biochemical Corporation). Degradation of the oligonucleotide was determined over time by reverse HPLC (WatersXBridge™ Shield RP18 Column 2.5 μm (3.0 mm×50 mm)). The employed buffer contained 50 mM Tris HCl (pH 8.0) and 10 mM MgCl2 (final concentration) and was sufficiently degassed before measurement. The condition of quantification by HPLC is as follows.
(HPLC Quantification Condition)
Mobile Phase:
Solution A: 0.1 M triethyl ammonium acetate buffer (pH 7.0)
Solution B: 0.1 M triethyl ammonium acetate buffer: acetonitrile=1:1 (v/v) (pH 7.0)
Gradient: 15%-21% solution B (16 min)
Column: WatersXBridge™ Shield RP18 Column 2.5 μm (3.0 mm×50 mm)
Flow rate: 0.8 mL/min
Column temperature: 50° C.
Detection: UV (254 nm)

The result was shown in FIG. 1. In FIG. 1, "Remaining oligonucleotides (%)" refers to the ratio of the undegraded oligonucleotides (10 mer) at the time of measurement to the undegraded oligonucleotides (10 mer) at the time 0.

As shown, the nucleotide (nature) and the nucleotide (LNA) are degraded completely in 40 minutes. The remaining ratio of the nucleotide (12) (Pyrazole BNA) after 40 minutes is 55%, while the remaining ratio of the nucleotide (5) (Triazole BNA) after 40 minutes is 80%. The remaining ratio of the oligonucleotide (17) (Tetrazole BNA) after 40 minutes is 100%. Therefore, the oligonucleotides of the present invention have much higher enzyme-resistance than the unmodified oligonucleotide and the oligonucleotide (LNA) prepared with the publicly known artificial nucleotides. Therefore, the oligonucleotides of the present invention have a very good in vivo persistence. Thus, the oligonucleotides of the present invention are useful as materials for synthesizing nucleic acid pharmaceuticals.

INDUSTRIAL APPLICABILITY

As shown in the above Examples, oligonucleotides prepared with a nucleotide(s) or nucleoside(s) of the present invention show the superior binding affinity to a single strand RNA and nuclease resistance. Therefore, such oligonucleotides have a very good in vivo persistence. Thus, the nucleosides or nucleotides of the present invention are useful very much as materials for synthesizing nucleic acid pharmaceuticals such as antisense oligonucleotide and the like.

The invention claimed is:
1. A compound of formula (I) or a salt thereof:

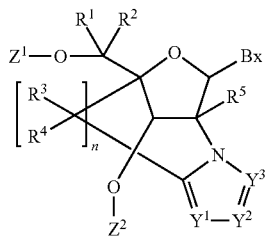

(I)

wherein
$Y^1$ is $CR^6$ or N,
$Y^2$ is $CR^7$ or N,
$Y^3$ is $CR^8$ or N,
$R^6$, $R^7$ and $R^8$ are each independently, a hydrogen atom, halogen, cyano, substituted or unsubstituted alkyl, substituted or unsubstituted alkenyl, substituted or unsubstituted alkynyl, substituted or unsubstituted amino, substituted or unsubstituted alkoxy, substituted or unsubstituted alkylcarbonylamino, substituted or unsubstituted alkenylcarbonylamino, substituted or unsubstituted alkynylcarbonylamino, substituted or unsubstituted alkylcarbamoyl, substituted or unsubstituted alkenylcarbamoyl, or substituted or unsubstituted alkynylcarbamoyl,
Bx is a nucleic acid base moiety,
$Z^1$ and $Z^2$ are each independently, a hydrogen atom, a hydroxyl protecting group or a reactive phosphorus group,
$R^1$ and $R^2$ are each independently, a hydrogen atom, halogen, cyano, substituted or unsubstituted alkyl, substituted or unsubstituted alkenyl, or substituted or unsubstituted alkynyl,
$R^3$ are each independently, a hydrogen atom, halogen, cyano, substituted or unsubstituted alkyl, substituted or unsubstituted alkenyl, or substituted or unsubstituted alkynyl,
$R^4$ are each independently, a hydrogen atom, halogen, cyano, substituted or unsubstituted alkyl, substituted or unsubstituted alkenyl, or substituted or unsubstituted alkynyl,
$R^5$ is a hydrogen atom, halogen, cyano, substituted or unsubstituted alkyl, substituted or unsubstituted alkenyl, or substituted or unsubstituted alkynyl, and
n is an integer of 0 to 3, and wherein when n=0, the 4'-position is bonded directly to the 2' ring.

2. The compound or salt thereof of claim 1, wherein a group of the formula:

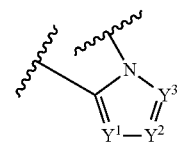

is a group of the formula:

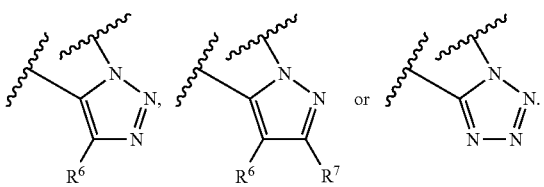

3. The compound or salt thereof of claim 1, wherein Bx is substituted or unsubstituted purin-9-yl, or substituted or unsubstituted 2-oxo-pyrimidin-1-yl.

4. The compound or salt thereof of claim 1, wherein $Z^1$ is a hydrogen atom or a hydroxyl protecting group.

5. The compound or salt thereof of claim 4, wherein the hydroxyl protecting group is acetyl, t-butyl, t-butoxymethyl, methoxymethyl, tetrahydropyranyl, 1-ethoxyethyl, 1-(2-chloroethoxy)ethyl, 2-trimethylsilylethyl, p-chlorophenyl, 2,4-dinitrophenyl, benzyl, benzoyl, p-phenylbenzoyl, 2,6-dichlorobenzyl, levulinoyl, diphenylmethyl, p-nitrobenzyl, trimethylsilyl, triethylsilyl, t-butyldimethylsilyl, t-butyldiphenylsilyl, triphenylsilyl, triisopropylsilyl, benzoyl formate, chloroacetyl, trichloroacetyl, trifluoroacetyl, pivaloyl, isobutyryl, 9-fluorenylmethyloxycarbonyl, methansulfonyl, p-toluenesulfonyl, trifluoromethanesulfonyl, trityl, monomethoxytrityl, dimethoxytrityl, trimethoxytrityl, 9-phenylxanthin-9-yl or 9-(p-methoxyphenyl)xanthin-9-yl.

6. The compound or salt thereof of claim 1, wherein $Z^2$ is a hydrogen atom or a reactive phosphorus group.

7. The compound or salt thereof of claim 6, wherein the reactive phosphorus group is diisopropylcyanoethoxy phosphoramidite or H-phosphonate.

8. An oligonucleotide comprising one or more nucleoside structure of formula (II) or a pharmaceutically acceptable salt thereof:

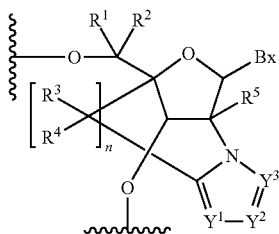

(II)

wherein
$Y^1$ is $CR^6$ or N,
$Y^2$ is $CR^7$ or N,
$Y^3$ is $CR^8$ or N,
$R^6$, $R^7$ and $R^8$ are each independently, a hydrogen atom, halogen, cyano, substituted or unsubstituted alkyl, substituted or unsubstituted alkenyl, substituted or unsubstituted alkynyl, substituted or unsubstituted amino, substituted or unsubstituted alkoxy, substituted or unsubstituted alkylcarbonylamino, substituted or unsubstituted alkenylcarbonyl amino, substituted or unsubstituted alkynylcarbonylamino, substituted or unsubstituted alkylcarbamoyl, substituted or unsubstituted alkenylcarbamoyl or substituted or unsubstituted alkynylcarbamoyl,
Bx is a nucleic acid base moiety,
$R^1$ and $R^2$ are each independently, a hydrogen atom, halogen, cyano, substituted or unsubstituted alkyl, substituted or unsubstituted alkenyl, or substituted or unsubstituted alkynyl,
$R^3$ are each independently, a hydrogen atom, halogen, cyano, substituted or unsubstituted alkyl, substituted or unsubstituted alkenyl, or substituted or unsubstituted alkynyl,
$R^4$ are each independently, a hydrogen atom, halogen, cyano, substituted or unsubstituted alkyl, substituted or unsubstituted alkenyl, or substituted or unsubstituted alkynyl,
$R^5$ is a hydrogen atom, halogen, cyano, substituted or unsubstituted alkyl, substituted or unsubstituted alkenyl, or substituted or unsubstituted alkynyl, and
n is an integer of 0 to 3, and when n=0, the 4'-position is bonded directly to the 2'ring.

9. The compound or salt thereof of claim 2, wherein Bx is substituted or unsubstituted purin-9-yl, or substituted or unsubstituted 2-oxo-pyrimidin-1-yl.

10. The compound or salt thereof of claim 2, wherein $Z^1$ is a hydrogen atom or a hydroxyl protecting group.

11. The compound or salt thereof of claim 3, wherein Z' is a hydrogen atom or a hydroxyl protecting group.

12. The compound or salt thereof of claim 10, wherein the hydroxyl protecting group is acetyl, t-butyl, t-butoxymethyl, methoxymethyl, tetrahydropyranyl, 1-ethoxyethyl, 1-(2-chloroethoxy)ethyl, 2-trimethylsilylethyl, p-chlorophenyl, 2,4-dinitrophenyl, benzyl, benzoyl, p-phenylbenzoyl, 2,6-dichlorobenzyl, levulinoyl, diphenylmethyl, p-nitrobenzyl, trimethylsilyl, triethylsilyl, t-butyldimethylsilyl, t-butyldiphenylsilyl, triphenylsilyl, triisopropylsilyl, benzoyl formate, chloroacetyl, trichloroacetyl, trifluoroacetyl, pivaloyl, isobutyryl, 9-fluorenylmethyloxycarbonyl, methansulfonyl, p-toluenesulfonyl, trifluoromethanesulfonyl, trityl, monomethoxytrityl, dimethoxytrityl, trimethoxytrityl, 9-phenylxanthin-9-yl or 9-(p-methoxyphenyl)xanthin-9-yl.

13. The compound or salt thereof of claim 11, wherein the hydroxyl protecting group is acetyl, t-butyl, t-butoxymethyl, methoxymethyl, tetrahydropyranyl, 1-ethoxyethyl, 1-(2-chloroethoxy)ethyl, 2-trimethylsilylethyl, p-chlorophenyl, 2,4-dinitrophenyl, benzyl, benzoyl, p-phenylbenzoyl, 2,6-dichlorobenzyl, levulinoyl, diphenylmethyl, p-nitrobenzyl, trimethylsilyl, triethylsilyl, t-butyldimethylsilyl, t-butyldiphenylsilyl, triphenylsilyl, triisopropylsilyl, benzoyl formate, chloroacetyl, trichloroacetyl, trifluoroacetyl, pivaloyl, isobutyryl, 9-fluorenylmethyloxycarbonyl, methansulfonyl, p-toluenesulfonyl, trifluoromethanesulfonyl, trityl, monomethoxytrityl, dimethoxytrityl, trimethoxytrityl, 9-phenylxanthin-9-yl or 9-(p-methoxyphenyl)xanthin-9-yl.

14. The compound or salt thereof of claim 2, wherein $Z^2$ is a hydrogen atom or a reactive phosphorus group.

15. The compound or salt thereof of claim 3, wherein $Z^2$ is a hydrogen atom or a reactive phosphorus group.

16. The compound or salt thereof of claim 4, wherein $Z^2$ is a hydrogen atom or a reactive phosphorus group.

17. The compound or salt thereof of claim 5, wherein $Z^2$ is a hydrogen atom or a reactive phosphorus group.

18. The compound or salt thereof of claim 14, wherein the reactive phosphorus group is diisopropylcyanoethoxy phosphoramidite or H-phosphonate.

19. The compound or salt thereof of claim 15, wherein the reactive phosphorus group is diisopropylcyanoethoxy phosphoramidite or H-phosphonate.

20. The compound or salt thereof of claim 16, wherein the reactive phosphorus group is diisopropylcyanoethoxy phosphoramidite or H-phosphonate.

* * * * *